US011131677B2

(12) United States Patent
Prasad et al.

(10) Patent No.: US 11,131,677 B2
(45) Date of Patent: Sep. 28, 2021

(54) METHODS FOR TREATING TESTOSTERONE DEFICIENCY IN MEN AND METHODS FOR PRECISE DOSING OF UGT2B17 SUBSTRATE DRUGS

(71) Applicant: University of Washington, Seattle, WA (US)

(72) Inventors: Bhagwat Prasad, Seattle, WA (US); Abdul Basit, Seattle, WA (US); Haeyoung Zhang, Seattle, WA (US); John K. Amory, Seattle, WA (US)

(73) Assignee: University of Washington, Seattle, WA (US)

( * ) Notice: Subject to any disclaimer, the term of this patent is extended or adjusted under 35 U.S.C. 154(b) by 44 days.

(21) Appl. No.: 16/380,876

(22) Filed: Apr. 10, 2019

(65) Prior Publication Data
US 2019/0307773 A1 Oct. 10, 2019

Related U.S. Application Data

(60) Provisional application No. 62/655,705, filed on Apr. 10, 2018.

(51) Int. Cl.
| | |
|---|---|
| *G01N 33/74* | (2006.01) |
| *A61K 31/5685* | (2006.01) |
| *A61K 31/192* | (2006.01) |
| *A61K 31/196* | (2006.01) |
| *A61K 31/506* | (2006.01) |
| *A61K 31/167* | (2006.01) |
| *A61P 5/26* | (2006.01) |
| *G01N 33/573* | (2006.01) |
| *A61K 31/4365* | (2006.01) |
| *A61K 9/00* | (2006.01) |

(52) U.S. Cl.
CPC ......... *G01N 33/743* (2013.01); *A61K 31/167* (2013.01); *A61K 31/192* (2013.01); *A61K 31/196* (2013.01); *A61K 31/4365* (2013.01); *A61K 31/506* (2013.01); *A61K 31/5685* (2013.01); *A61P 5/26* (2018.01); *G01N 33/573* (2013.01); *A61K 9/0053* (2013.01); *C12Y 204/01017* (2013.01); *G01N 2333/91102* (2013.01); *G01N 2800/52* (2013.01)

(58) Field of Classification Search
CPC ............ G01N 33/743; G01N 2800/52; C12Y 204/01017
See application file for complete search history.

(56) References Cited

U.S. PATENT DOCUMENTS

| | | | |
|---|---|---|---|
| 6,287,834 B1 | 9/2001 | Belanger et al. | |
| 2002/0165195 A1 | 11/2002 | Wang et al. | |
| 2003/0203043 A1 | 10/2003 | Yegorova | |
| 2003/0215462 A1 | 11/2003 | Wacher et al. | |
| 2011/0033856 A1* | 2/2011 | Lazarus | C12Q 1/48 435/6.17 |

FOREIGN PATENT DOCUMENTS

| | | |
|---|---|---|
| JP | 2011190267 A | 9/2011 |
| WO | 2011/017696 A2 | 2/2011 |

OTHER PUBLICATIONS

Hu, Androgen and Estrogen Receptors in Breast Cancer Coregulate Human UDP-Glucuronosyltransferases 2B15 and 2B17, Cancer Res, 2016, 76(19), pp. 5881-5893. (Year: 2016).*
Rigiacciol, GPER is involved in the stimulatory effects of aldosterone in breast cancer cells and breast tumor-derived endothelial cells, Oncotarget, 2015, 7(1), pp. 94-111. (Year: 2015).*
Shoskes, J.J., et al., "Pharmacology of Testosterone Replacement Therapy Preparations," Translational Andrology and Urology 5(6):834-843, Dec. 2016.
Snyder, P.J., et al., "Effects of Testosterone Treatment in Older Men," New England Journal of Medicine 374(7):611-624, Feb. 2016.
Sten, T., et al., "Non-Steroidal Anti-Inflammatory Drugs Interact With Testosterone Glucuronidation," Steroids 74(12):971-977, Nov. 2009.
Sten, T., et al., "UDP-Glucuronosyltransferases (UGTs) 2B7 and UGT2617 Display Converse Specificity in Testosterone and Epitestosterone Glucuronidation, Whereas UGT2A1 Conjugates Both Androgens Similarly," Drug Metabolism and Disposition 37(2):417-423, Feb. 2009.
Strahm, E., et al., "Dose-Dependent Testosterone Sensitivity of the Steroidal Passport and GC-C-IRMS Analysis in Relation to the UGT2B17 Deletion Polymorphism," Drug Testing and Analysis 7(11-12):1063-1070, Nov.-Dec. 2015.
Sun, D., et al., "Characterization of 17-Dihydroexemestane Glucuronidation: Potential Role of the UGT2B17 Deletion in Exemestane Pharmacogenetics," Pharmacogenetics and Genomics 20(10):575-585, Oct. 2010.
Swanson, C., et al., "The Uridine Diphosphate Glucuronosyltransferase 2B15 $D^{85}Y$ and 2B17 Deletion Polymorphisms Predict the Glucuronidation Pattern of Androgens and Fat Mass in Men," Journal of Clinical Endocrinology & Metabolism 92(12):4878-4882, Dec. 2007.
Takeyama, J., et al., "17β-Hydroxysteroid Dehydrogenase Type 1 and 2 Expression in the Human Fetus," Journal of Clinical Endocrinology & Metabolism 85(1):410-416, Jan. 2000.
Tanner, J.-A., et al., "Predictors of Variation in CYP2A6 mRNA, Protein, and Enzyme Activity in a Human Liver Bank: Influence of Genetic and Nongenetic Factors," Journal of Pharmacology and Experimental Therapeutics 360(1):129-139, Jan. 2017.

(Continued)

*Primary Examiner* — Theodore R. Howell
(74) *Attorney, Agent, or Firm* — Christensen O'Connor Johnson Kindness PLLC

(57) ABSTRACT

Treatment of testosterone deficiency in men by a precision medicine approach using a biomarker of activity of UGT2B17 that is involved in testosterone urinary elimination. By inhibiting UGT2B17, alone or in combination with administration of testosterone, testosterone deficiency in men can be treatable. Further, a method of dose selection for precise dosing of UGT2B17 substrate drugs is provided. Additionally, methods for safe dosing of pharmaceutical agents that undergo UGT2B17-mediated acyl glucuronidation are provided.

5 Claims, 33 Drawing Sheets

(56) References Cited

OTHER PUBLICATIONS

Täuber, U., et al., "Absolute Bioavailability of Testosterone After Oral Administration of Testosterone-Undecanoate and Testosterone," European Journal of Drug Metabolism and Pharmacokinetics 11(2):145-149, Apr.-Jun. 1986.

Tax, L., letter to the editor, European Journal of Drug Metabolism and Pharmacokinetics 12(3):225-226, 1987.

Thummel, K.E., et al., "Enzyme-Catalyzed Processes of First-Pass Hepatic and Intestinal Drug Extraction," Advanced Drug Delivery Reviews 27(2-3):99-127, Sep. 1997.

Thummel, K.E., "Gut Instincts: CYP3A4 and Intestinal Drug Metabolism," Journal of Clinical Investigation 117(11):3173-3176, Nov. 2007.

Tria, A., et al., "Steroid 5α-Reductase 1 Polymorphisms and Testosterone/Dihydrotestosterone Ratio in Male Patients With Hypospadias," Hormone Research 61(4):180-183, 2004.

Uddin, M., et al., "UGT2B17 Copy Number Gain in a Large Ankylosing Spondylitis Multiplex Family," BMC Genetics 14:67, Aug. 2013, 6 pages.

Urano, T., et al., "Association of a Single Nucleotide Polymorphism in the Constitutive Androstane Receptor Gene With Bone Mineral Density," Geriatrics Gerontology International 9(3):235-241, Sep. 2009.

Usmani, K.A., and J. Tang, "Human Cytochrome P450: Metabolism of Testosterone by CYP3A4 and Inhibition by Ketoconazole," Current Protocols in Toxicology 20(1):4-13, May 2004.

Vaughan, E.D., Jr., "Long-Term Experience With 5-a-Reductase Inhibitors," Reviews in Urology 5(4):S28-S33, 2003.

Verreault, M., et al., "Regulation of Endobiotics Glucuronidation by Ligand-Activated Transcription Factors: Physiological Function and Therapeutic Potential," Drug Metabolism Reviews 42(1):110-122, Feb. 2010.

Vidal, A.C., et al., "Novel Associations of UDP-Glucuronosyltransferase 2B Gene Variants With Prostate Cancer Risk in a Multiethnic Study," BMC Cancer 13:556, Nov. 2013, 15 pages.

Vigen, R., et al., "Association of Testosterone Therapy With Mortality, Myocardial Infarction, and Stroke in Men With Low Testosterone Levels," Journal of the American Medical Association 310(17):1829-1836, Nov. 2013.

Vrana, M., et al., "Database of Optimized Proteomic Quantitative Methods for Human Drug Disposition-Related Proteins for Applications in Physiologically Based Pharmacokinetic Modeling," CPT: Pharmacometrics & Systems Pharmacology 6(4):267-276, Apr. 2017.

Wang, Y.-H., et al., "UGT2B17 Genetic Polymorphisms Dramatically Affect the Pharmacokinetics of MK-7246 in Healthy Subjects in a First-in-Human Study," Clinical Pharmacology & Therapeutics 92(1):96-102, Jul. 2012.

Wang, C., et al., "Low Testosterone Associated With Obesity and theMetabolic Syndrome Contributes to Sexual Dysfunction and Cardiovascular Disease Risk in Men With Type 2 Diabetes," Diabetes Care 34:1669-1675, Jul. 2011.

Wells, P.G., et al., "Glucuronidation and the UDP-Glucuronosyltransferases in Health and Disease," Drug Metabolism and Disposition 32(3):281-290, Mar. 2004.

Wijayakumara, D.D., et al., "Regulation of Human UGT2B15 and UGT2B17 by miR-376c in Prostate Cancer Cell Lines," Journal of Pharmacology and Experimental Therapeutics 354:417-425, Sep. 2015.

Wong, N.-S., et al., "Impact of UDP-Gluconoryltransferase 2B17 Genotype on Vorinostat Metabolism and Clinical Outcomes in Asian Women With Breast Cancer," Pharmacogenetics and Genomics 21(11):760-768, Nov. 2011.

Wong, S., et al., "Utility of Pooled Cryopreserved Human Enterocytes as an in Vitro Model for Assessing Intestinal Clearance and Drug-Drug Interactions," Drug Metabolism Letters 12(1):3-13, 2018.

Wu, F.C.W., et al., "Identification of Late-Onset Hypogonadism in Middle-Aged and Elderly Men," New England Journal of Medicine 363(2):123-135, Jul. 2010.

Wurzel, R., et al., "The Effect of Dutasteride on Intraprostatic Dihydrotestosterone Concentrations in Men With Benign Prostatic Hyperplasia," Prostate Cancer and Prostatic Diseases 10(2):149-154, 2007.

Xu, M., et al., "Genetic and Nongenetic Factors Associated With Protein Abundance of Flavin-Containing Monooxygenase 3 in Human Liver," Journal of Pharmacology and Experimental Therapeutics 363:265-274, Nov. 2017.

Xue, Y., et al., "Adaptive Evolution of UGT2B17 Copy-Number Variation," American Journal of Human Genetics 83:337-346, Sep. 2008.

Yang, T.-L., et al., "Genome-Wide Copy-Number-Variation Study Identified a Susceptibility Gene, UGT2B17, for Osteoporosis," American Journal of Human Genetics 83:663-674, Dec. 2008.

Yuan, L.-M., et al., "Inter-Isoform Hetero-Dimerization of Human UDP-Glucuronosyltransferases (UGTs) 1A1, 1A9, and 2B7 and Impacts on Glucuronidation Activity," Scientific Reports 6:34450, 2016, pp. 1-17.

Zhang, N., et al., "Drug-Drug Interaction Potentials of Tyrosine Kinase Inhibitors via Inhibition of UDP-Glucuronosyltransferases," Scientific Reports 5:17778, 2015, pp. 1-10.

Zhang, H., et al., "Quantitative Characterization of UDP-Glucuronosyltransferase 2B17 in Human Liver and Intestine and Its Role in Testosterone First-Pass Metabolism," Biochemical Pharmacology 156:32-42, Oct. 2018.

Zhang, H., "Is UGT2B17 the Rate-Determining Enzyme for Testosterone Glucuronidation?" PowerPoint Presentation, n.d., University of Washington Pharmaceutics, Seattle, 16 pages.

Zhu, A.Z.X., et al., "Genetic and Phenotypic Variation in UGT2B17, a Testosterone-Metabolizing Enzyme, is Associated With Body Mass Index in Males," Pharmacogenetics and Genomics 25(5):263-269, May 2015. (Author Manuscript provided, PMCID: PMC4382380, available in PMC May 1, 2016, 14 pages).

Westaby, D., et al., "Liver Damage From Long-Term Methyltestosterone," The Lancet 310(8032):261-263, Aug. 1977.

Ho, M.-C.D., et al., "Human Enterocytes as an In Vitro Model for the Evaluation of Intestinal Drug Metabolism: Characterization of Drug-Metabolizing Enzyme Activities of Cryopreserved Human Enterocytes From Twenty-Four Donors," Drug Metabolism and Disposition 45(6):686-691, Jun. 2017.

Hong, B.S., and T.Y. Ahn, "Recent Trends in the Treatment of Testosterone Deficiency Syndrome," International Journal of Urology 14(11):981-985, Nov. 2007.

Hu, D.G., et al., "Androgen and Estrogen Receptors in Breast Cancer Coregulate Human UDP-Glucuronosyltransferases 2B15 and 2B17," Cancer Research 76(19):5881-5393, Oct. 2016.

Hu, D.G., et al., "A Novel Polymorphism in a Forkhead Box A1 (FOXA1) Binding Site of the Human UDP Glucuronosyltransferase 2B17 Gene Modulates Promoter Activity and Is Associated with Altered Levels of Circulating Androstane-3α,17β-diol Glucuronide," Molecular Pharmacology 78(4):714-722, Oct. 2010.

Jakobsson, J., et al., "Large Differences in Testosterone Excretion in Korean and Swedish Men Are Strongly Associated With a UDP-Glucuronosyl Transferase 2B17 Polymorphism," Journal of Clinical Endocrinology & Metabolism 91(2):687-693, Feb. 2006.

Jenkinson, C., et al., "Dietary Green and White Teas Suppress UDP-Glucuronosyltransferase UGT2B17 Mediated Testosterone Glucuronidation," Steroids 77(6):691-695, May 2012.

Jenkinson, C., et al., "Effects of Dietary Components on Testosterone Metabolism via UDP-Glucuronosyltransferase," Frontiers in Endocrinology, vol. 4, Article 80, Jul. 2013, pp. 1-4.

Ji, J.-Z., et al., "Human UGT2B7 is the Major Isoform Responsible for the Glucuronidation of Clopidogrel Carboxylate," Biopharmaceutics & Drug Disposition 39(2):88-98, Feb. 2018.

Jones, C.R., et al., "Gut Wall Metabolism. Application of Pre-Clinical Models for the Prediction of Human Drug Absorption and First-Pass Elimination," AAPS Journal 18(3):589-603, May 2016.

(56) References Cited

OTHER PUBLICATIONS

Kahma, H., et al., "Clopidogrel Carboxylic Acid Glucuronidation is Mediated Mainly by UGT2B7, UGT2B4, and UGT2B17: Implications for Pharmacogenetics and Drug-Drug Interactions," Drug Metabolism and Disposition 46(2):141-150, Feb. 2018.
Karypidis, A.-H., et al., "Deletion Polymorphism of the UGT2B17 Gene is Associated With Increased Risk for Prostate Cancer and Correlated to Gene Expression in the Prostate," Pharmacogenomics Journal 8(2):147-151, Apr. 2008.
Kaufman, J.M., and A. Vermeulen, "The Decline of Androgen Levels in Elderly Men and Its Clinical and Therapeutic Implications," Endocrine Reviews 26(6):833-876, Oct. 2005.
Kpoghomou, M.-A., et al., "UGT2B17 Polymorphism and risk of Prostate Cancer: A Meta-Analysis," ISRN Oncology 2013:465916, 2013, 7 pages.
Kumar, P., et al., "Male Hypogonadism: Symptoms and Treatment," Journal of Advanced Pharmaceutical Technology & Research 1(3):297-301, Jul.-Sep. 2010.
Labrie F., et al., "The Key Role of 17β-Hydroxysteroid Dehydrogenases in Sex Steroid Biology," . Steroids 62(1):148-158, Jan. 1997.
Lazarus, P., et al., "Genotype-Phenotype Correlation Between the Polymorphic UGT2B17 Gene Deletion and NNAL Glucuronidation Activities in Human Liver Microsomes," Pharmacogenetics and Genomics 15(11):769-778, Nov. 2005.
Luo, S., et al., "Role of the UGT2B17 Deletion in Exemestane Pharmacogenetics," Pharmacogenomics Journal 18(2):295-300, Apr. 2018. (Author Manuscript provided, PMCID: PMC5700874, available in PMC Apr. 29, 2018, 15 pages.).
Luo, S., et al., "Role of the UGT2B17 Deletion in Exemestane Pharmacogenetics," Pharmacogenomics Journal 18(2):295-300, Apr. 2018.
Markle, J.G.M., et al., "Sex Differences in the Gut Microbiome Drive Hormone-Dependent Regulation of Autoimmunity," Science 339(6123)1084-1088, Mar. 2013.
Martín-Escudero, P., et al., "Impact of UGT2B17 Gene Deletion on the Steroid Profile of an Athlete," Physiological Reports 3(12):e12645, 2015, 7 pages.
Mazer, N., et al., "Comparison of the Steady-State Pharmacokinetics, Metabolism, and Variability of a Transdermal Testosterone Patch Versus a Transdermal Testosterone Gel in Hypogonadal Men," Journal of Sex Medicine 2(2):213-226, Mar. 2005.
Miettinen, M.M., et al., "Human 17b-Hydroxysteroid Dehydrogenase Type 1 and Type Isoenzymes Have Opposite Activities in Cultured Cells and Characteristic Cell- and Tissue-Specific Expression," Biochemical Journal 314(Pt 3):839-845, Mar. 1996.
Miyauchi, E., et al., "Quantitative Atlas of Cytochrome P450, UDP-Glucuronosyltransferase, and Transporter Proteins in Jejunum of Morbidly Obese Subjects," Molecular Pharmaceutics 13(8):2631-2640, Aug. 2016.
Morales, A., et al., "A Practical Guide to Diagnosis, Management and Treatment of Testosterone Deficiency for Canadian Physicians," Canadian Urological Association Journal 4(4):269-275, Aug. 2010.
Mulligan, T., et al., "Prevalence of Hypogonadism in Males Aged at Least 45 Years: The HIM Study," International Journal of Clinical Practice 60(7):762-769, Jul. 2006.
Neumann, E., et al., "Age-Dependent Hepatic UDP-Glucuronosyltransferase Gene Expression and Activity in Children," Frontiers in Pharmacology, vol. 7, Article 437, Nov. 2016, 7 pages.
Nieschlag, E., et al., "Plasma Androgen Levels in Men After Oral Administration of Testosterone or Testosterone Undecanoate," Acta Endocrinologica 79(2):366-374, Jun. 1975.
Oda, S., et al., "A Comprehensive Review of UDP-Glucuronosyltransferase and Esterases for Drug Development," Drug Metabolism and Pharmacokinetics 30(1):30-51, Feb. 2015.
Ohtsuki, S., et al., "Simultaneous Absolute Protein Quantification of Transporters, Cytochromes P450, and UDP-Glucuronosyltransferases as a Novel Approach for the Characterization of Individual Human Liver: Comparison With mRNA Levels and Activities," Drug Metabolism and Disposition 40(1):83-92, Jan. 2012.

Okano, M., et al., "UDP-Glucuronosyltransferase 2B17 Genotyping in Japanese Athletes and Evaluation of the Current Sports Drug Testing for Detecting Testosterone Misuse," Drug Testing and Analysis 5(3):166-181, Mar. 2013.
Pâquet, S., et al., "Differential Expression of the Androgen-Conjugating UGT2B15 and UGT2B17 Enzymes in Prostate Tumor Cells During Cancer Progression," Journal of Clinical Endocronology and Metabolism 97(3):E428-E432, Mar. 2012.
Pastuszak, A.W., et al., "Comparison of the Effects of Testosterone Gels, Injections, and Pellets on Serum Hormones, Erythrocytosis, Lipids, and Prostate-Specific Antigen," Sexual Medicine 3(3):165-173, Sep. 2015.
Pavlatos, A.M., et al., "Review of Oxymetholone: A 17α-Alkylated Anabolic-Androgenic Steroid," Clinical Therapeutics 23(6):789-801, Jun. 2001.
Pearce, R.E., et al., "Developmental Expression of CYP2B6: A Comprehensive Analysis of mRNA Expression, Protein Content and Bupropion Hydroxylase Activity and the Impact of Genetic Variation," Drug Metabolism and Disposition 44(7):948-958, Jul. 2016.
Ponce, O.J., et al., "The Efficacy and Adverse Events of Testosterone Replacement Therapy in Hypogonadal Men: A Systematic Review and Meta-Analysis of Randomized, Placebo-Controlled Trials," Journal of Clinical Endocronology and Metabolism 103(5):1745-1754, May 2018.
Prasad, B., "Precision Approaches in Oral Testosterone Replacement Therapy (TRT)," PowerPoint Presentation, n.d., University of Washington, School of Pharmacy, Seattle, 7 pages.
Prasad, B., et al., "Interindividual Variability in Hepatic Organic Anion-Transporting Polypeptides and P-Glycoprotein (ABCB1) Protein Expression: Quantification by Liquid Chromatography Tandem Mass Spectroscopy and Influence of Genotype, Age, and Sex," Drug Metabolism and Disposition 42:78-88, Jan. 2014.
Prasad, B., et al., "Ontogeny of Hepatic Drug Transporters as Quantified by LC-MS/MS Proteomics," Clinical Pharmacology and Therapeutics 100(4):362-370, Oct. 2016. (Author Manuscript provided, PMCID: PMC5017908, available in PMC Oct. 1, 2017, 20 pages.).
Rao, G.S., et al., "Studies on a Testosterone Glucuronyltransferase From the Cytosol Fraction of Human Liver," Biochemical Journal 119(4):635-642, Oct. 1970.
Riches, Z., et al., "Quantitative Evaluation of the Expression and Activity of Five Major Sulfotransferases (SULTs) in Human Tissues: The SULT 'Pie'," Drug Metabolism and Disposition 37(11):2255-2261, Nov. 2009.
Sadeque, A.J.M., et al., "Identification of Human UDP-Glucuronosyltransferases Involved in N-Carbamoyl Glucuronidation of Lorcaserin," Drug Metabolism and Disposition 40(4):772-778, Apr. 2012.
Sandberg, A.A., and W.R. Slaunwhite, Jr., "Metabolism of 4-$C_{14}$-Testosterone in Human Subjects. I. Distribution in Bile, Blood, Feces and Urine," Journal of Clinical Investigation 35(12):1331-1339, Dec. 1956.
Sano, T., et al., "17B-Hydroxysteroid Dehydrogenase Type 2 Expression and Enzyme Activity in the Human Gastrointestinal Tract," Clinical Science 101(5):485-491, Nov. 2001.
Sato, Y., et al., "Optimized Methods for Targeted Peptide-Based Quantification of Human Uridine 5'-Diphosphate-Glucuronosyltransferases in Biological Specimens Using Liquid Chromatography—Tandem Mass Spectrometry," Drug Metabolism and Disposition 42(5):885-889, May 2014.
Schedl, H.P., "Absorption of Steroid Hormones From the Human Small Intestine," Journal of Clinical Endocrinology and Metabolism 25(10):1309-1316, Oct. 1965.
Schiffer, L., et al., "Intracrine Androgen Biosynthesis, Metabolism and Action Revisited," Molecular and Cellular Endocrinology 465:4-26, Apr. 2018.
Schulze, J.J., et al., "Doping Test Results Dependent on Genotype of Uridine Diphospho-Glucuronosyl Transferase 2B17, the Major Enzyme for Testosterone Glucuronidation," Journal of Clinical Endocrinology and Metabolism 93(7)2500-2506, Jul. 2008.

(56) References Cited

OTHER PUBLICATIONS

Schweizer, M.T., et al., "Effect of Bipolar Androgen Therapy for Asymptomatic Men With Castration-Resistant Prostate Cancer: Results From a Pilot Clinic Study," Science: Translational Medicine 7(269):269ra2, Jan. 2015, 12 pages.

Shin, H.-C., et al., "Comparative Gene Expression of Intestinal Metabolizing Enzymes," Biopharmaceutics & Drug Disposition 30(8):411-421, Nov. 2009.

Shirasaka, Y., et al., "Interindividual Variability of CYP2C19-Catalyzed Drug Metabolism Due to Differences in Gene Diplotypes and Cytochrome P450 Oxidoreductase Content," Pharmacogenomics Journal 16(4):375-387, Aug. 2016.

Amory, J.K., and W.J. Bremner, "Oral Testosterone in Oil Plus Dutasteride in Men: A Pharmacokinetic Study," Journal of Clinical Endocrinology & Metabolism 90(5):2610-2617, May 2005.

Angstadt, A.Y., et al., "The Effect of Copy Number Variation (CNV) in the Phase II Detoxification Genes, UGT2B1 and UGT2B28, on Colorectal Cancer Risk," Cancer 119(13):2477-2485, Jul. 2013. (Author Manuscript provided, PMCID: PMC3686841, available in PMC Jul. 1, 2014, 14 pages.).

Araujo, A.B., et al., "Prevalence and Incidence of Androgen Deficiency in Middle-Aged and Older Men: Estimates from the Massachusetts Male Aging Study," Journal of Clinical Endocrinology & Metabolism 89(12):5920-5926, Dec. 2004.

Auchus, M.L., and R.J. Auchus, "Human Steroid Biosynthesis for the Oncologist," Journal of Investigative Medicine 60(2):495-503, Feb. 2012.

Bao, B.-Y., et al., "Androgen Receptor Mediates the Expression of UDP-Glucuronosyltransferase 2 B15 and B17 Genes," Prostate 68(8):839-848, Jun. 2008. (Author Manuscript provided, PMCID: PMC2703184, available in PMC Jun. 29, 2009, 16 pages.).

Barbier, O., and A. Bélanger, "Inactivation of Androgens by UDP-Glucuronosyltransferases in the Human Prostate," Best Practice & Research Clinical Endocrinology & Metabolism 22(2):259-270, Apr. 2008.

Basit, A., et al., "Effect of Dose and 5α-Reductase Inhibition on the Circulating Testosterone Metabolite Profile of Men Administered Oral Testosterone," Clinical and Translational Science 11(5):513-522, Sep. 2018.

Bassil, N., et al., "The Benefits and Risks of Testosterone Replacement Therapy: A Review," Therapeutics and Clinical Risk Management 5(3):427-448, Jun. 2009.

Beaulieu, M., et al., "Isolation and Characterization of a Novel cDNA Encoding a Human UDP-Glucuronosyltransferase Active on $C_{19}$ Steroids," Journal of Biological Chemistry 271(37):22855-22862, Sep. 1996.

Bhasin, S., et al., "Effect of Testosterone Supplementation With and Without aDual 5α-Reductase Inhibitor on Fat-FreeMass in Men With Suppressed Testosterone Production," Journal of the American Medical Association 307(9):931-939, Mar. 2012.

Bhasin, S., et al., "Contributors to the Substantial Variation in On-Treatment Testosterone Levels in Men Receiving Transdermal Testosterone Gels in Randomized Trials," Andrology 6(1):151-157, Jan. 2018.

Bhatt, D.K., et al., "Hepatic Abundance and Activity of Androgen- and Drug-Metabolizing Enzyme UGT2B17 Are Associated With Genotype, Age, and Sex," Drug Metabolism and Disposition 46(6):888-896, Jun. 2018.

Bhatt, D.K., et al., "Age-Dependent Protein Abundance of Cytosolic Alcohol and Aldehyde Dehydrogenases in Human Liver," Drug Metabolism and Disposition 45(9):1044-1048, Sep. 2017.

Bhatt, D.K., and B. Prasad, "Critical Issues and Optimized Practices in Quantification of Protein Abundance Level to Determine Interindividual Variability in DMET Proteins by LC-MS/MS Proteomics," Clinical Pharmacology & Therapeutics 103(4):619-630, Apr. 2018.

Bhoi, S., et al., "UGT2B17 Expression: A Novel Prognostic Marker Within IGHV-Mutated Chronic Lymphocytic Leukemia?" Haematologica 101:e65, 2016, 3 pages.

Bremner, W.J., "Testosterone Deficiency and Replacement in Older Men," New England Journal of Medicine 363(2):189-191, Jul. 2010.

Burgess, K.S., et al., "Age-Related Changes in microRNA Expression and Pharmacogenes in Human Liver," Clinical Pharmacology & Therapeutics 98(2):205-215, Aug. 2015. (Author Manuscript provided, PMCID: PMC4512918, available in PMC Aug. 1, 2016, 21 pages.).

Busch, D., et al., "LC-MS/MS Method for the Simultaneous Quantification of Intestinal CYP and UGT Activity," Journal of Pharmaceutical and Biomedical Analysis 155:194-201, Jun. 2018.

Cai, L., et al., "Prostate Cancer With Variants in CYP17 and UGT2B17 Genes: A Meta-Analysis," Protein & Peptide Letters 19(1):62-69, Jan. 2012.

Cheetham, T.C., et al., "Association of Testosterone Replacement With Cardiovascular Outcomes Among Men With Androgen Deficiency," JAMA Internal Medicine 177(4):491-499, Apr. 2017.

Chen, G., et al., "Association Between Glucuronidation Genotypes and Urinary NNAL Metabolic Phenotypes in Smokers," Cancer Epidemiology, Biomarkers & Prevention 25(7):1175-1184, Jul. 2016. (Author Manuscript provided, pmcid: PMC5087993, available in PMC Jul. 1, 2017, 23 pages.).

Chen, S.M., et al., "Impact of UGT2B17 Gene Deletion on the Pharmacokinetics of 17-hydroexemestane in Healthy Volunteers," Journal of Clinical Pharmacology 56(7):875-884, Jul. 2016. (Author Manuscript provided, PMCID: PMC4882280, available in PMC Jul. 1, 2017, 18 pages.).

Chew, S., et al., "Homozygous Deletion of the UGT2B17 Gene is Not Associated With Osteoporosis Risk in Elderly Caucasian Women," Osteoporosis International 22(6):1981-1986, Jun. 2011. (Author Manuscript provided, PMCID: PMC3605783, available in PMC Mar. 22, 2013, 9 pages.).

Clavell-Hernández, J., and R. Wang, "Emerging Evidences in the Long Standing Controversy Regarding Testerone Replacement Therapy and Cardiovascular Events," World Journal of Men's Health 36(2):92-102, May 2018.

Corona, G., et al., "Emerging Medication for the Treatment of Male Hypogonadism," Expert Opinion on Emerging Drugs 17(2):239-259, Jun. 2012.

Court, M.H., et al., "UDP-Glucuronosyltransferase (UGT) 2B15 Pharmacogenetics: UGT2B15 D85Y Genotype and Gender Are Major Determinants of Oxazepam Glucuronidation by Human Liver," Journal of Pharmacology and Experimental Therapeutics 310(2):656-665, Aug. 2004.

Daggett, P.R., et al., "Oral Testosterone, a Reappraisal," Hormone Research 9(3):121-129, 1978.

Day, J.M., et al., "Design and Validation of Specific Inhibitors of 17β-Hydroxysteroid Dehydrogenases for Therapeutic Application in Breast and Prostate Cancer, and in Endometriosis," Endocrine-Related Cancer 15(3):665-692, Sep. 2008.

Drozdzik, M., et al., "Protein Abundance of Clinically Relevant Drug-Metabolizing Enzymes in the Human Liver and Intestine: A Comparative Analysis in Paired Tissue Specimens," Clinical Pharmacology & Therapeutics 104(3):515-524, Sep. 2018.

Du, Q.-Q., et al., "PXR Polymorphisms and Their Impact on Pharmacokinetics/Pharmacodynamics of Repaglinide in Healthy Chinese Volunteers," European Journal of Clinical Pharmacology 69(11):1917-1925, Nov. 2013.

Ekström, L., et al., "Tissue Distribution and Relative Gene Expression of UDP-Glucuronosyltransferases (2B7, 2B15, 2B17) in the Human Fetus," Drug Metabolism and Disposition 41(2):291-295, Feb. 2013.

Fallon, J.K., et al., "Targeted Quantitative Proteomics for the Analysis of 14 UGT1As and -2Bs in Human Liver Using NanoUPLC-MS/MS With Selected Reaction Monitoring," Journal of Proteome Research 12(10):4402-4413, Oct. 2013.

Farthing, M.J.G., et al., "Testosterone Metabolism by the Rat Gastrointestinal Tract, In Vitro and In Vivo," Gut 23(3):226-234, Mar. 1982.

Franchimont, P., et al., "Effects of Oral Testosterone Undecanoate in Hypogonadal Male Patients," Clinical Endocrinology 9(4):313-320, Endocrinology 9(4):313-320, Oct. 1978.

(56) References Cited

OTHER PUBLICATIONS

Frey, H., et al., "Bioavailability of Oral Testosterone in Males," European Journal of Clinical Pharmacology 16(5):345-349, Nov. 1979.

Futterweit, W., et al., "Testosterone in Human Urine," Steroids 4(1):137-145, Jul. 1964.

Gallagher, C.J., et al., "The UGT2I317 Gene Deletion Polymorphism and Risk of Prostate Cancer: A Case-Control Study in Caucasians," Cancer Detection and Prevention 31(4):310-315, 2007.

Gallagher, C.J., et al., "Sex Differences in UDP-Glucuronosyltransferase 2B17 Expression and Activity," Drug Metabolism and Disposition 38(12):2204-2209, Dec. 2010.

Gauthier-Landry, L., et al., "Multiple Roles for UDP-Glucuronosyltransferase (UGT)2B15 and UGT2B17 Enzymes in Androgen Metabolism and Prostate Cancer Evolution," Journal of Steroid Biochemistry and Molecular Biology 145:187-192, Jan. 2015.

Ghayee, H.K., and R.J. Auchus, "Basic Concepts and Recent Developments in Human Steroid Hormone Biosynthesis," Reviews in Endocrine and Metabolic Disorders 8(4):289-300, Dec. 2007.

Golds, G., et al., "Male Hypogonadism and Osteoporosis: The Effects, Clinical Consequences, and Treatment of Testosterone Deficiency in Bone Health," International Journal of Endocrinology 2017:4602129, 2017, 15 pages.

Gooren, L.J.G., "A Ten-Year Safety Study of the Oral Androgen Testosterone Undecanoate," Journal of Andrology 15(3):212-215, May/Jun. 1994.

Gordon, A.S., et al., "PGRNseq: A Targeted Capture Sequencing Panel for Pharmacogenetic Research and Implementation," Pharmacogenetics and Genomics 26(4):161-168, Apr. 2016.

Gröer, C., et al., "Absolute Protein Quantification of Clinically Relevant Cytochrome P450 Enzymes and UDP-Glucuronosyltransferases by Mass Spectrometry-Based Targeted Proteomics," Journal of Pharmaceutical and Biomedical Analysis 100:393-401, Nov. 2014.

Gruber, M., et al., "Overexpression of Uridine Diphospho Glucuronosyltransferase 2B17 in High-Risk Chronic Lymphocytic Leukemia," Blood 121(7):1175-1183, Feb. 2013.

Guay, A.T., et al., "Clomiphene Increases Free Testosterone Levels in Men With Both Secondary Hypogonadism and Erectile Dysfunction: Who Does and Does Not Benefit?" International Journal of Impotence Research 15(3):156-165, Jun. 2003.

Guillemette, C., "Pharmacogenomics of Human UDP-Glucuronosyltransferase Enzymes," Pharmacogenomics Journal 3(3):136-158, Jun. 2003.

Hamada, A., et al., "Effect of SLCO1B3 Haplotype on TestosteroneTransport and Clinical Outcome in Caucasian Patients With Androgen-Independent Prostatic Cancer," Clinical Cancer Research 14(11):3312-3318, Jun. 2008.

Herbst, K.L., et al., "A Single Dose of the Potent Gonadotropin-Releasing Hormone Antagonist Acyline Suppresses Gonadotropins and Testosterone for 2 Weeks in Healthy Young Men," Journal of Clinical Endocrinology & Metabolism 89(12):5959-5965, Dec. 2004.

Hirata, H., et al., "Function of UDP-Glucuronosyltransferase 2B17 (UGT2B17) is Involved in Endometrial Cancer," Carcinogenesis 31(9):1620-1626, Sep. 2010.

* cited by examiner

*Fold change in matabolite levels after oral 200 and 800 mg T (T200 and T800) with respect base line*

| Metabolite | T200 | T800 |
|---|---|---|
| T | 0.3 | 0.8 |
| TG | 78.4 | 276.8 |
| DHT | 0.6 | 2.2 |
| DGTG | 7.5 | 40.6 |
| A | 1.2 | 5.5 |
| AG | 9.5 | 29.7 |
| Etio | 0.8 | 3.5 |
| EtioG | 13.0 | 39.5 |
| AED | 2.3 | 14.9 |

0.1 mg/mL HLM + 0.1 mg/mL Alamethicin + 1 μM Testosterone + 0.01% BSA 15 min preincubation at 37 °C 2.5 mM UDPGA 30 min incubation at 37 °C LC-MS/MS Analysis

| Protein abundance (pmol/mg microsomal protein) | | |
|---|---|---|
| | UGT2B17 High expressor | UGT2B Non-Expressor (del/del) |
| UGT2B17 | 5.53 | BLOQ |
| UGT2B15 | 15.82 | 25.12 |

FIG. 10
*(CONT.)*

METHODS FOR TREATING TESTOSTERONE DEFICIENCY IN MEN AND METHODS FOR PRECISE DOSING OF UGT2B17 SUBSTRATE DRUGS

CROSS-REFERENCE TO RELATED APPLICATION

This application claims the benefit of U.S. Provisional Application No. 62/655,705, filed Apr. 10, 2018, the disclosure of which is expressly incorporated herein by reference in its entirety.

STATEMENT OF GOVERNMENT LICENSE RIGHTS

This invention was made with government support under Grant No. R01 HD081299 awarded by the National Institutes of Health. The government has certain rights in the invention.

BACKGROUND

Testosterone (T) is the key male sex-hormone. T plays an indispensable role in the development of male reproductive system during fetal life, and triggers the development of secondary sexual characteristics at puberty and maintains sexual function and bone and muscle health during adulthood. Low concentrations of T can occur for a variety of reasons. Men with low T experience fatigue, depression, diminished libido, loss of muscle strength, osteoporosis, visceral obesity, and insulin resistance. T-replacement therapy (TRT) is the first-line treatment for T deficiency and has been shown to improve bone density, alleviate depression and maintain sexual function. Currently available options for TRT in the United States (US) include intramuscular injections, transdermal patches and gels. The development of an oral TRT has been extremely challenging because of extensive first pass metabolism. As a result, the 2-4 million hypogonadal men in the US requiring TRT mainly rely on intra-muscular or topical T dosage forms, both of which are challenging in terms of compliance, and have sub-optimal pharmacokinetics (PK) or variable absorption. Clearly, the development of a safe and effective formulation of oral T is a major unmet need for these men.

Oral T is readily absorbed from small intestine by diffusion in humans, but the absorbed T dose is metabolized in both the intestine and the liver before reaching to the circulation, resulting in a very poor bioavailability of 2-8%. Exogenously administered T is metabolized to multiple unconjugated and conjugated metabolites, where the major urinary metabolites are glucuronide conjugates which are formed in the liver and intestine by various human UDP-glucuronosyl transferases (UGTs). In particular, UGT2B17 is the major T-glucuronidation enzyme. UGT2B17 is of interest as it is highly polymorphic and copy number variations (CNVs) in its gene are associated with multiple potentially T-related pathologies, e.g., obesity, prostate cancer, osteoporosis, ankylosing spondylitis, and endometrial cancer. UGT2B17 is highly expressed in the intestine and the liver and leads to formation of acyl glucuronide metabolites, which are often associated with hepatotoxicity or extra-hepatic toxicity of pharmaceutical agents.

Thus, because of UGT2B17 high variability, there is a need for a biomarker that can identify and stratify individuals who would experience greater levels of UGT2B17-mediated acyl glucuronides formation than others and allow precise, individualized dosing of oral testosterone and other pharmaceutical agents which are subject to UGT2B17-mediated metabolism.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, provided herein is a method for treating testosterone deficiency in a subject, comprising the steps of:
  obtaining a sample from a subject suspected of having testosterone deficiency;
  determining the presence in the sample of one or more biomarkers of UGT2B17 activity;
  identifying an effective therapeutic amount of one or more agents for treating testosterone deficiency; and
  administering the effective therapeutic amount of the agent to treat testosterone deficiency in the subject in need thereof.

In some embodiments, the one or more biomarkers of UGT2B17 activity is a normalized testosterone glucuronide (normalized TG), for example, a ratio of concentration of testosterone glucuronide (TG) to concentration of aldosterone glucuronide (AG), a ratio of concentration of testosterone glucuronide (TG) to concentration of etiocholanolone glucuronide (EG), a ratio of concentration of testosterone glucuronide (TG) to concentration of testosterone sulfate (TS), a ratio of concentration of testosterone glucuronide (TG) to concentration of hydroxyl-testosterone, or a ratio of concentration of testosterone glucuronide TG to concentration of epitestosterone glucuronide (epiT). In some embodiments, the sample is blood, urine, plasma, or serum.

In some embodiments, the one or more agents for treating testosterone deficiency comprises orally administered testosterone, an inhibitor of UGT2B17, such as ibuprofen, diclofenac, or imatinib, or a combination of orally administered testosterone with one or more UGT2B17 inhibitors.

In another aspect, provided herein is a method for treating a subject with a pharmaceutical agent that is metabolized by UGT2B17-dependent acyl glucuronidation, comprising the steps of:
  obtaining a sample from a subject;
  quantifying one or more biomarkers of UGT2B17 activity in the sample, such as normalized TG;
  identifying an effective therapeutic amount of a pharmaceutical agent that is metabolized by UGT2B17-dependent acyl glucuronidation; and
  administering the effective therapeutic amount of the pharmaceutical agent to the subject in need thereof.

In some embodiments, the effective therapeutic amount is an amount that does not result in hepatotoxicity caused by UGT2B17 mediated acyl-glucuronidation in the subject.

In yet another aspect, provided herein is a method for testing an individual for testosterone doping, the method comprising:
  (a) obtaining a biological sample from an individual subject to testosterone doping testing;
  (b) determining a ratio of testosterone glucuronide (TG) to aldosterone glucuronide (AG) in the biological sample; and (c) comparing the ratio of testosterone glucuronide (TG) to aldosterone glucuronide (AG) in the sample with that from a retention sample.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 2D represents fold change in the respective metabolites at T200 and T800 in experimental hypogonadism subjects as compared to the eugonadal subjects. Glucuronides (TG, AG and EtioG) are the major circulating metabolites.

FIG. 3A depicts pharmacokinetic profiles of T and its primary (TG, DHT and AED) and secondary (A, AG, Etio and EtioG) metabolites after single oral dose (200 mg) of T with (dotted line) and without (solid line) dutasteride co-administration. Dots represent mean plasma concentration at individual sampling time-points and bars represent standard error (SE). FIG. 3B demonstrates the effect of co-administered dutasteride on the levels of T metabolites in the pooled serum indicating fold change at T200 and T800. FIG. 3C demonstrates the effect of dutasteride co-treatment on the levels of DHT, A and AG in human hepatocyte culture. Data for FIGS. 3B and 3C were analyzed using Paired t-test, p value<0.01, *p value<0.001.

FIGS. 5A-5C represent the correlation between UGT2B17 protein expression in HLM and glucuronidation activity toward T, A, and Etio, respectively. FIGS. 5D-5F represent the correlation between UGT2B7 protein expression in HLM and glucuronidation activity toward T, A, and Etio, respectively. FIG. 5G represent glucuronidation activity of recombinant human UGT2B enzymes towards T, A, and Etio at 1 µM. FIGS. 5H and 5I are estimated glucuronidation activity of UGT2Bs towards T, A and Etio in the human liver and the intestinal microsomes. The scaling was based on UGT2B protein abundance in the liver (36.6, 21.2, and 0.92 pmol/mg, unpublished data) and the intestine (2.83, 0.0, and 8.87 pmol/mg) for UGT2B7, UGT2B15 and UGT2B17, respectively.

DETAILED DESCRIPTION

Figure 1:
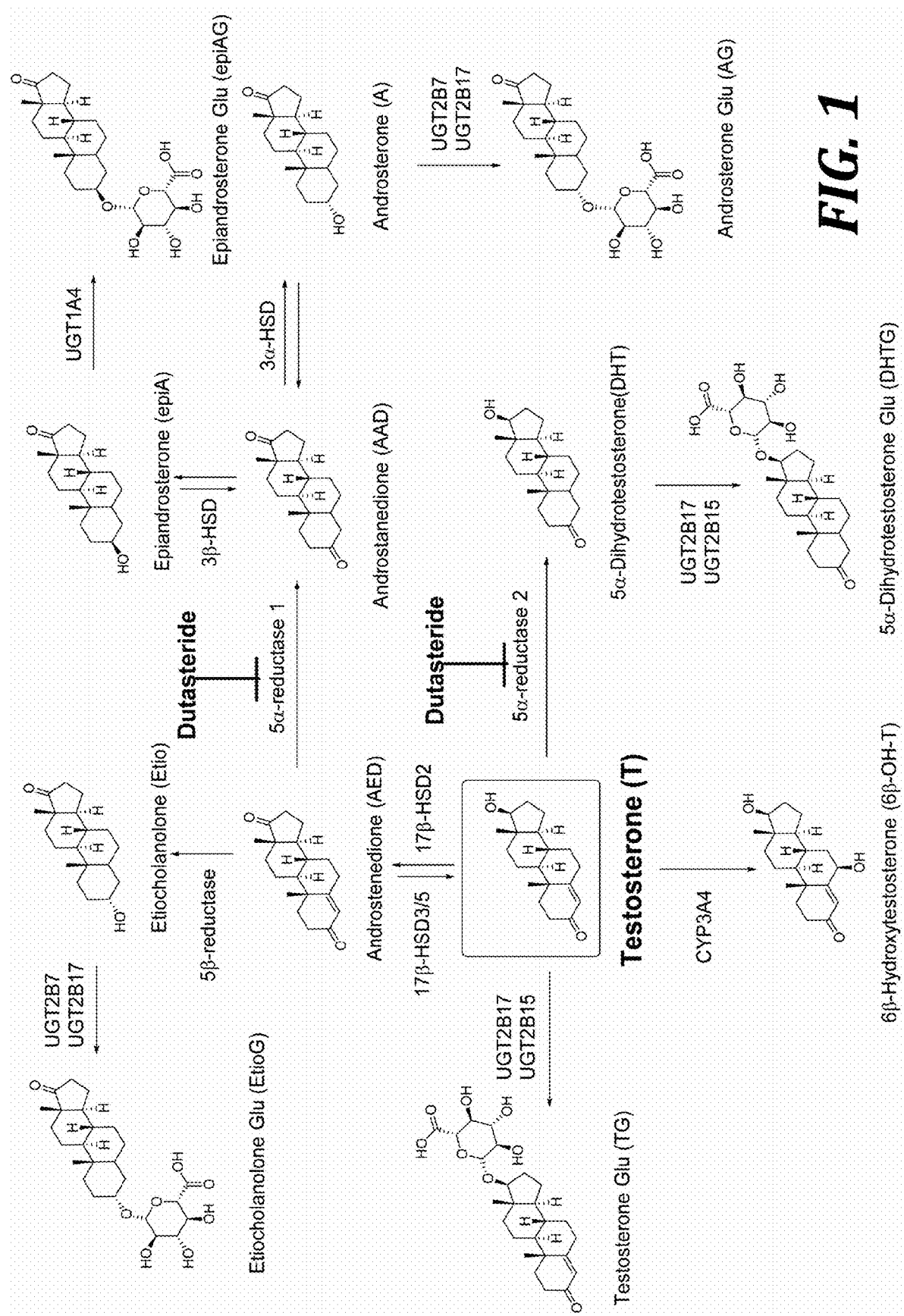
FIG. 1 shows major metabolite pathways of T disposition in vivo. All these metabolites were quantified by targeted metabolomics analysis. T is conjugated by UGT2B15 and UGT2B17 to T glucuronide (TG). T is also converted to dihydrotestosterone (DHT), AED and 6β-hydroxytestosterone (6β-OH-T) by 5-AR2, 17β-HSD2 and CYP3A4, respectively. AED is then metabolized to number of sequential metabolites, etiocholanolone (Etio), androstanedione, androsterone (A) and epiandrosterone (epiA). Both A and Etio are conjugated by UGT2B7 and UGT2B17 to A glucuronide (AG) and Etio glucuronide (EtioG) while epiA is glucuronidated by UGT1A4 to epiA glucuronide. All these metabolites (except epiA, epiAG and 6β-OH-T) were quantifiable in both 200 and 800 mg dose in following relative order: AG>TG>EtioG>AED>A>T>DHT>Etio. Dutasteride is a dual inhibitor of 5-AR1 and 5-AR2. Sulfate conjugates were not analyzed in this study.

The disclosure addresses treating testosterone deficiency in men using a precision medicine approach. Based on the analysis of human samples, the inventors have identified that a critical enzyme UGT2B17, which is involved in testosterone elimination, is highly variable in men and have subsequently identified a specific UGT2B17 biomarker as described below.

Thus, in one aspect, the disclosure provides a method for treating testosterone deficiency in a subject, comprising the steps of:

obtaining a sample from a subject suspected of having testosterone deficiency;

determining the presence in the sample of one or more biomarkers of UGT2B17 activity;

identifying an effective therapeutic amount of one or more agents for treating testosterone deficiency; and administering the effective therapeutic amount of the agent to treat testosterone deficiency in the subject in need thereof.

In some embodiments, the one or more biomarkers of UGT2B17 activity is a phenotypical biomarker. In some embodiments, the one or more biomarkers of UGT2B17 activity is a normalized testosterone glucuronide (normalized TG). In some embodiments, normalized TG is a ratio of the concentration of TG to the concentration of another T metabolite, for example, aldosterone glucuronide (AG), in a sample. As discussed below, in some embodiments, the normalized TG can be a ratio of concentration of testosterone glucuronide (TG) to concentration of aldosterone glucuronide (AG), a ratio of concentration of testosterone glucuronide (TG) to concentration of etiocholanolone glucuronide (EG), a ratio of concentration of testosterone glucuronide (TG) to concentration of testosterone sulfate (TS), a ratio of concentration of testosterone glucuronide (TG) to concentration of hydroxyl-testosterone, or a ratio of concentration of testosterone glucuronide TG to concentration of epitestosterone glucuronide (epiT). In some embodiments, normalized TG is a ratio of concentrations of TG and aldosterone glucuronide (AG), in a sample. In certain embodiments, a molar ratio of testosterone glucuronide (TG) to aldosterone glucuronide (AG) is used as a biomarker of UGT2B17 activity.

Any suitable sample can be used in the methods disclosed herein. In some embodiments, the sample is a biological sample selected from blood, urine, plasma, or serum. The determining of the presence of one or more biomarkers of UGT2B17 activity in the sample can be done by any method that is sufficiently sensitive to detect the presence of one or more biomarkers of UGT2B17 activity. In some embodiments, the method includes liquid chromatography and mass spectrometry. In some embodiments, the method includes LC/MS or LC-MS/MS. In some embodiments, the method comprises extracting one or more testosterone metabolites, such as TG, AG, EpiT, and the like, from the biological sample, for example, by solid phase extraction. In some embodiments, the method comprises separation of one or more testosterone metabolites by liquid chromatography, such as gradient liquid chromatography. In some embodiments, the determining the presence in the sample of one or more biomarkers of UGT2B17 activity comprises reverse phase liquid chromatography. Detection and/or quantification of the concentration of one or more testosterone metabolites, such as TG, AG, EpiT can be done by any suitable method, for example, by tandem mass spectrometry or MS/MS. In some embodiments, determining the presence in the sample of one or more biomarkers of UGT2B17 activity comprises the use of one or more internal standards.

In some embodiments, the one or more agents for treating testosterone deficiency comprise testosterone. In some embodiments, testosterone is administered orally for instance, as a pharmaceutical formulation comprising one or more excipients. Any suitable oral formulation of testosterone can be used in the methods of the disclosure. For example, in some embodiments, the testosterone is formulated for gastroretentive dosage. In some embodiments, the methods use gastroretentive formulations of testosterone. As used herein, gastroretentive formulations include formulations designed to remain in the stomach for a prolonged and predictable period of time. Consequently, gastric residence time of drug substances, such as testosterone, is extended and their bioavailability improved. Non-limiting examples of gastroretentive drug delivery approaches include co-administration of drugs or pharmaceutical excipients influencing gastric motility pattern and thereby delaying gastric emptying process, magnetic systems, mucoadhesive systems, size-increasing systems due to swelling or unfolding, density-controlled systems that either float on gastric contents or sediment, and combination systems.

In some embodiments, the amount of normalized TG in an individual's biological sample can be used to determine the therapeutically effective oral dose of testosterone for the subject. In some embodiments, the dose is proportional to the amount of the one or more biomarkers of UGT2B17 activity, for example, a ratio of TG/AG.

In some embodiments, the one or more agents for treating testosterone deficiency comprise an inhibitor of UGT2B17. Any suitable inhibitor of UGT2B17 can be used in the methods of the disclosure. For example, in some embodiments, the inhibitor of UGT2B17 activity comprises a nonsteroidal anti-inflammatory drug (NSAID) or a small molecule kinase inhibitor. Useful NSAIDs include ibuprofen, diclofenac, and combinations thereof. In some embodiments, the inhibitor of UGT2B17 is imatinib. In some embodiments, the inhibitor of UGT2B17 activity is co-administered with testosterone. Co-administration of one or more therapeutic agents, as used herein, includes administration of one or more pharmaceutical agents simultaneously, for example, in a single formulation, and sequentially.

In another aspect, provided herein are methods of reducing hepatotoxcicity and/or adverse effects of pharmaceutical agents that undergo UGT2B17-dependent acyl glucuronidation. Thus, the disclosure provides a method for treating a subject with a pharmaceutical agent that undergoes UGT2B17-dependent acyl glucuronidation, comprising the steps of:

obtaining a sample from a subject;

determining the presence of one or more biomarkers of UGT2B17 activity in the sample;

identifying an effective therapeutic amount of a pharmaceutical agent; and administering the effective therapeutic amount of the pharmaceutical agent to the subject in need thereof.

UGT2B17-mediated metabolism of certain pharmaceutical agents generally leads to formation of acyl glucuronides which are often associated with hepatotoxicity or extrahepatic toxicity of the parent pharmaceutical agents. For example, diclofenac forms acyl glucuronide which leads to its toxicity, and an individual with high UGT2B17 is expected to form higher diclofenac glucuronide that will eventually lead to greater toxicity of diclofenac. Because UGT2B17 is highly variable, a suitable biomarker, such as normalized TG, that identifies individuals who would experience greater levels of acyl glucuronide than others, can allow personalization of dosing of such pharmaceutical agents.

In some embodiments, the methods disclosed herein can be used in drug development, for example, to predict and/or pre-empt potential toxicity of a pharmaceutical agent in clinical trials. In some embodiments, the methods disclosed herein can be used to identify individuals with a greater risk of adverse drug-drug interactions. Acyl glucuronides are known to inactivate another drug metabolizing enzyme, Cytochrome P450 2C8 (CYP2C8), which is involved in metabolism of certain pharmaceutical agents. For example, clopidogrel is an antiplatelet drug that is metabolized to clopidogrel acid glucuronide (CAG) by UGT2B17. CAG is a potent inactivator of CYP2C8 and thus leads to increased plasma concentration of CYP2C8 substrates (e.g., repaglinide, pioglitazone, rosiglitazone, and cerivastatin), in clinic when co-administered. In particular, increased cerivastatin levels have been shown to be associated with rhabdomyolysis and even deaths, resulting withdrawal of this drug from market in early 2000, which was primarily observed in patients taking drugs such as gemfibrozil and clopidogrel, both of which form acyl glucuronides. Therefore, the UGT2B17 phenotypic biomarker, for example, normalized TG, can identify individuals with greater risks to such drug-interactions.

In some embodiments of the methods disclosed herein, the pharmaceutical agent is an agent that undergoes UGT2B17-dependent acyl glucuronidation. In certain embodiments, the pharmaceutical agent is selected from the group consisting of vorinostat, exemestane, and clopidogrel.

As described above, any suitable biological sample can be used, such as blood, urine, plasma, or serum. In some embodiments, the sample is urine.

In some embodiments, the determining the presence of one or more biomarkers of UGT2B17 activity in the sample is done by LC-MS/MS as described above.

In certain embodiments, the one or more biomarkers of UGT2B17 activity is a phenotypical biomarker. In some embodiments, the one or more biomarkers of UGT2B17 activity is normalized testosterone glucuronide (normalized TG), for example, a ratio of concentration of testosterone glucuronide (TG) to concentration of aldosterone glucuronide (AG), a ratio of concentration of testosterone glucuronide (TG) to concentration of etiocholanolone glucuronide (EG), a ratio of concentration of testosterone glucuronide (TG) to concentration of testosterone sulfate (TS), a ratio of concentration of testosterone glucuronide (TG) to concentration of hydroxyl-testosterone, or a ratio of concentration of testosterone glucuronide TG to concentration of epitestosterone glucuronide (epiT). In some embodiments, normalized TG is a ratio of concentrations of TG and aldosterone glucuronide (AG) in a sample. In certain embodiments, a molar ratio of testosterone glucuronide (TG) to aldosterone glucuronide (AG) is used as a biomarker of UGT2B17 activity.

As used herein, the effective therapeutic amount is an amount of a pharmaceutical agent that does not result in hepatotoxicity caused by UGT2B17 mediated acyl-glucuronidation of the pharmaceutical in the subject.

In yet another aspect, the disclosure provides a method for testing a biological sample for testosterone doping, comprising: obtaining a biological sample from a subject and determining the amount of normalized TG in the biological sample. In some embodiments, the methods further comparing the amount of normalized T with that from a control or a retention sample.

Testosterone doping is typically tested by measuring the total testosterone in urine, which is primarily (about 90%) testosterone glucuronide (TG). Because TG is formed via UGT2B17-mediated glucuronidation of T, variability in this enzyme leads to variable test outcomes. For example, UGT2B17 high expressers show higher total urinary TG levels, which can result in a false positive doping test. Similarly, low expression of UGT2B17 in an individual can lead to false negative test results. Because of these reasons, some testosterone doping tests rely on TG/EpiTG to address individual variability. However, TG/EpiTG has poor sensitivity, and a testosterone doping test that accounts for an individual UGT2B17 activity is highly desirable. Thus, in some embodiments, the testosterone doping tests disclosed herein comprise determining a molar ratio of testosterone glucuronide (TG) to aldosterone glucuronide (AG) in a sample, for example, a urine sample, which can be done by any suitable method as described above.

In another aspect, the disclosure provides a method for identification of individuals with greater risk to UGT2B17-associated diseases (e.g., chronic lymphocytic leukemia, osteoporosis, and prostate cancer) and tobacco carcinogenicity by determining normalized TG (e.g., TG/AG) in a biological sample obtained from the individuals suspected to have greater risk of UGT2B17-associated diseases. It has been shown that UGT2B17 gene deletion is associated with chronic lymphoid leukemia (CLL), prostate cancer, and osteoporosis. However, these results are controversial because of the high non-genetic variability in UGT2B17. Thus, using a phenotypic biomarker of UGT2B17 such as the normalized TG (e.g., TG/AG) as disclosed herein, susceptibility to CCL can be predicted.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

When further clarity is required, the term "about" has the meaning reasonably ascribed to it by a person skilled in the art when used in conjunction with a stated numerical value or range, denoting somewhat more or somewhat less than the stated value or range, to ±10% of the stated value.

Notwithstanding that the numerical ranges and parameters setting forth the broad scope of the invention are approximations, the numerical values set forth in the specific examples are reported as precisely as possible. It is understood that any numerical value, however, inherently contains certain errors necessarily resulting from the standard deviation found in their respective testing measurements.

The following examples are presented for the purpose of illustrating, not limiting, the invention.

EXAMPLES

A. Effect of Dose and 5α-Reductase Inhibition on the Circulating Testosterone Metabolite Profile of Men Administered Oral Testosterone Development of an oral testosterone (T) therapy has proven extremely challenging because of extensive and variable first-pass metabolism. The in vivo metabolism of T with increasing oral doses of T, both alone and with the co-administration of dutasteride (5α-reductase inhibitor) by LC-MS/MS are described herein.

Method.

Seven healthy male volunteers with mean age 24.2±8.7 years were recruited. T emulsion in sesame oil, mixed with milk, was administered orally to human subjects with acyline-induced experimental hypogonadism. The blood samples were collected and the serum was isolated and stored in −80° C. Steroids and their metabolites were extracted from serum using protein precipitation followed by solid-phase extraction and analyzed by UPLC coupled with SCIEX 6500 MS/MS.

Result.

In eugonadal men prior to dosing, the circulating concentration of T, androstenedione (A), etiocholanolone-glucuronide (EtioG), and androsterone-glucuronide (AG) was 8.6, 20.9, 9.1, and 55.3%, respectively, of the total T-related species, whereas T-glucuronide (TG) was ~1%. When T was dosed orally to men with experimental hypogonadism, a proportion of T-glucuronide increased to 13%. Dutasteride treatment significantly decreased levels of androsterone and its metabolites.

Conclusion.

Extensive metabolism of orally dosed T to androsterone glucuronide via androstenedione was revealed, with T-glucuronide appearing to be the second most important metabolite. This information is of importance in the development of an effective oral T therapy and has implications for T doping research.

Oral T is readily absorbed from small intestine by diffusion in humans, but the absorbed T dose is metabolized in both the intestine and the liver before reaching to the circulation, resulting in a very poor bioavailability of 2-8%. Exogenously administered T has previously been reported to be metabolized to multiple unconjugated and conjugated metabolites (FIG. 1), where the major urinary metabolites are glucuronide conjugates which are formed in the liver and intestine by various human UDP-glucuronosyl transferases (UGTs). In particular, UGT2B17 is the major T-glucuronidation enzyme. UGT2B17 is of interest as it is highly polymorphic and copy number variations (CNVs) in its gene are associated with multiple potentially T related pathologies, e.g., obesity, prostate cancer, osteoporosis, ankylosing spondylitis, and endometrial cancer. UGT2B17 is highly expressed in the intestine and the liver. Because of this and its known role in T metabolism, it has been hypothesized that the first pass-metabolism of T by UGT2B17 is the main reason for its poor or variable bioavailability. Therefore, to investigate the quantitative contribution of glucuronidation in the in vivo metabolism of T, the inventors quantified the serum levels of T and its downstream conjugated and unconjugated metabolites in subjects with acyline-induced experimental hypogonadism, who were administered oral T alone or with the 5α-reductase (5-AR) inhibitor, dutasteride. The inventors also compared the circulating metabolite profile after T-treatment with the physiological serum profile of healthy individuals. UGT2B17 polymorphisms also pose a significant challenge in detection of T doping by athletes, where metabolite ratios are used to create individual biological passports. Therefore, to test if the T metabolite ratios are dose-independent, the inventors quantified complete T metabolite panel after treating with two oral doses (200 and 800 mg).

Other than UGTs, 17β-HSD2, 5-AR, CYP3A4, and sulfotransferases (SULTs) can also metabolize T, however, the quantitative contribution of these enzymes in T first-pass metabolism is unknown. Dutasteride is a selective inhibitor of the type 1 and type 2 isoforms of the 5-AR enzyme (FIG. 1). The effect of dutasteride on T and DHT serum level have been previously reported, but its impact on the circulating T metabolite profile has not been characterized. To fill this knowledge gap, the inventors quantified the effect of dutasteride on T metabolite profile at 200 and 800 mg T oral doses.

Materials and Methods

LC-MS/MS grade acetonitrile, methanol, chloroform and formic acid were purchased from Fisher scientific (Fair Lawn, N.J., USA). Un-conjugated and conjugated steroid standards were purchased from Cerilliant corporation (Round Rock, Tex.) and Steraloid (Newport, R.I.). Recombinant human UGT2B7, UGT2B15, and UGT2B17 supersomes were purchased from Corning Life Science (Corning, N.Y.), and dutasteride for the in vitro experiments was from Sigma Aldrich (St. Louis, Mo.). Iodoacetamide (IAA), dithiothreitol (DTT), and pierce trypsin protease (MS grade) were purchased from Thermo Fisher Scientific (Rockford, Ill.). Ammonium bicarbonate buffer (ABC, 98% purity) was purchased from Acros Organics (Geel, Belgium). Human serum albumin (HSA) and bovine serum albumin (BSA) were obtained from Calbiochem (Billerica, Mass.) and Thermo Fisher Scientific (Rockford, Ill.), respectively. Surrogate peptides were produced by Thermo Fisher Scientific (Rockford, Ill.). UDPGA and MgCl2 were purchased from Sigma-Aldrich (St. Louis, Mo.). Hepatocyte were provided gratis by Lonza Inc (Walkersville, Md.), hepatocyte thawing media (UCRM™), hepatocyte plating media (UPCM™), hepatocyte induction media (HIM™) and hepatocyte quantification media (HQM™) were procured from IVAL LLC (Columbia, Md.).

For targeted T metabolomics study, previously collected and stored samples from seven subjects who received oral T, were used. Clinical study design is discussed below. All subjects provided written, informed consent prior to any study procedures. The study was approved by the University of Washington (UW) Investigational Review Board Committee. The oral T in sesame oil was manufactured by the compounding pharmacy at the UW, micronized T (U.S.P. grade, Spectrum Quality Projects, Gardena, Calif.) was suspended at 100 mg/ml in sesame oil (N.F. grade, Spectrum Quality Projects) and mixed thoroughly to create a homogenous T plus sesame oil emulsion. The emulsion was vigorously mixed by shaking with milk and administered to the subject. The drug exposure period lasted 11 days. On day 0, subjects received a single injection of the gonadotropin-releasing hormone (GnRH) antagonist acyline (300 μg/kg, subcutaneous), which has been shown to suppress T production in normal men for a minimum of 15 days. After one, two, and three days of acyline administration, subjects were given 200, 400, or 800 mg T-orally. Subjects self-administered dutasteride purchased by the University of Washington investigational pharmacy (0.5 mg, orally, once daily) on day 5-10 after acyline injection, and doses of T were repeated on days 8, 9, and 10, respectively. After each dose of T, subjects had blood drawn via a heparin-locked intravenous line at 0.5, 1, 2, 4, 6, 8, 10, 12, and 24 h for measurement of serum T and its unconjugated and conjugated metabolites. Serum was obtained from the blood by centrifugation and stored in −80° C. freezer until analysis by LC-MS/MS.

Serum was pooled from control subjects (before acyline dose, baseline) and from all time points after single oral dose of T at 200 mg (T200) and 800 mg (T800). While study was conducted with 200, 400 and 800 mg T dose, only T200 and T800 were quantified. T and its metabolites were extracted from the human serum sample using a protein precipitation with ice cold methanol (containing internal standard mix, Table 1) followed by solid-phase extraction (SPE) in C18 HLB cartridges (Waters). Calibration curve (CC), quality control (QC), or test samples (500 μL) were transferred to 5 mL micro-centrifuge tube. Protein precipitation was carried out using a 1:4 by volume methanol (2 ml) containing internal standard mix. Samples were mixed for 1 min by vortex mixing, and then centrifuged for 10 min at 3500×g at 4° C. The supernatant was transferred to glass tubes and dried under nitrogen evaporator. The resulting dried residue was re-dissolved in 2 mL of 5% methanol containing 0.2% formic acid and was used for SPE. The SPE cartridges were mounted on the positive pressure manifold and activated with 2 mL methanol and conditioned with 2 mL 0.2% formic acid. Samples (2 mL) were loaded onto the cartridges and flow through was discarded. Samples were washed with 1 mL of 5% methanol containing 0.2% formic acid to get rid of hydrophilic impurities. T metabolites were then eluted with 2 mL of methanol and collected in glass tubes. The eluate was then dried under nitrogen evaporator and reconstituted with 0.1 mL methanol:water (1:1, v/v) for LC-MS/MS analysis.

LC-MS/MS analyses were carried out on SCIEX 6500 triple quadrupole mass spectrometer coupled to a Waters Acquity UPLC system. Chromatographic separation of steroid metabolites was achieved using a reversed phase HSS T3 C18 column (2.1×100 mm, 1.8μ particle size). Mobile phase consisted of 0.1% formic acid in water (A) and 0.1% formic acid in acetonitrile (B) was used. The LC gradient system is reported in Table 2. All the MRM transitions and mass spectrometry parameters are reported in Table 2. Data were acquired by Analyst 1.6 software. LC-MS/MS method was validated for linearity, precision, accuracy, extraction efficiency, and auto-sampler stability.

TABLE 2

Validated LC-MS/MS method used for analysis of glucuronide metabolites (testosterone and DHT), and progesterone (internal standard).

LC gradient program (in vitro incubation for testosterone, DHT and progesterone)
ACQUITY UPLC ® BEH C18 column (2.1 × 50 mm, 1.7 μm)

| Time (min) | Flow rate (ml/min) | Water with 0.1% formic acid, % | Acetonitrile with 0.1% formic acid, % |
|---|---|---|---|
| 0 | 0.25 | 97 | 3 |
| 0.5 | 0.25 | 97 | 3 |
| 2.0 | 0.25 | 45 | 55 |
| 3.2 | 0.25 | 20 | 80 |
| 3.4 | 0.25 | 20 | 80 |
| 3.5 | 0.25 | 97 | 3 |
| 5.0 | 0.25 | 97 | 3 |

MS Parameters

| Peptide type | Parent ion (m/z) | Product ion (m/z) | CE (eV) | DP (V) |
|---|---|---|---|---|
| Testosterone | 289.2 | 97.1 | 30 | 80 |
| | | 109.1 | 30 | 80 |
| Testosterone-glucuronide | 465.1 | 97.1 | 25 | 70 |
| | | 109.1 | 25 | 70 |
| DHT | 291.4 | 255.2 | 28 | 106 |
| | | 159.1 | 36 | 106 |
| | | 91.1 | 84 | 106 |
| | | 291.4 | 5 | 106 |
| DHT-glucuronide | 467.26 | 255.2 | 25 | 70 |
| | | 159.1 | 31 | 70 |
| | | 291.3 | 25 | 70 |
| Progesterone (internal standard) | 315.2 | 109.1 | 30 | 70 |
| | | 97.1 | 30 | 70 |
| Testosterone-glucuronide-d3 | 465.2 | 289.2 | 25 | 70 |
| | | 271.2 | 30 | 70 |
| DHT-glucuronide-d3 | 470.2 | 294.2 | 30 | 80 |
| | | 276.2 | 30 | 80 |

HLM samples were isolated from 9 individual liver tissues from the University of Washington, School of Pharmacy liver bank and quantified for UGT2B7, UGT2B15 and UGT2B17 protein abundance using a validated trypsin digestion protocol (Vrana, M., Whittington, D., Nautiyal, V. & Prasad, B. Database of Optimized Proteomic Quantitative Methods for Human Drug Disposition-Related Proteins for Applications in Physiologically Based Pharmacokinetic Modeling. *CPT Pharmacometrics Syst Pharmacol* 6, 267-76 (2017), the disclosure of which is incorporated herein by reference). Glucuronidation activity assay was performed in HLM (0.1 mg/ml total protein) or recombinant human UGTs (10 μg/ml total protein) containing 5 mM $MgCl_2$-100 mM phosphate buffer at pH 7.4, alamethicin (0.1 mg/ml), BSA (0.02%) and substrate, T/A/Etio (1 μM to 10 μM). The reaction mixture was incubated for 15 min on ice to allow alamethicin pore formation. Reaction was initiated by adding UDPGA (2.5 mM) and incubating for 30 minutes at 37° C. The reaction was quenched by acetonitrile containing internal standard and the sample were centrifuged at 2000× g, 4° C. for 5 min. The supernatant was analyzed by LC-MS/MS to quantify substrate depletion and glucuronide formation.

Fractional contribution of each UGTs in the glucuronidation of androgens in the intestinal and liver microsomes using the protein abundance data was also extrapolated, and the in vitro in vivo extrapolation (IVIVE) approach discussed elsewhere. Briefly, intestine and liver abundance of UGT2B7, UGT2B15 and UGT2B17 of 2.83, 0.0 and 8.87 vs. 36.6, 21.2, and 0.92 pmol/mg microsomal proteins, respectively were considered for IVIVE of recombinant data to liver and intestinal microsomes.

Results

Figure 2A:
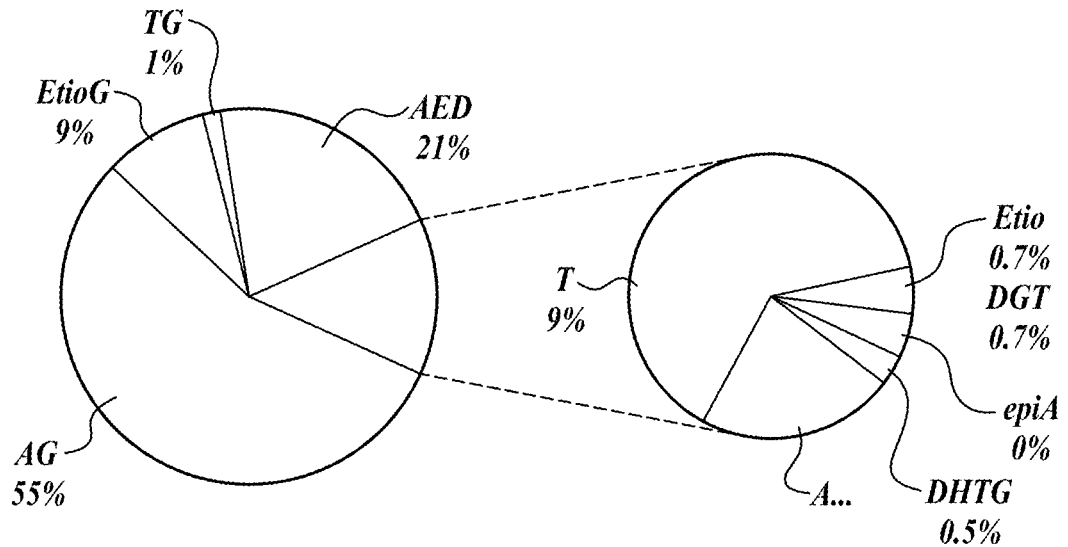
FIGS. 2A-2D show quantitative profile of circulating T, and its primary and secondary metabolites in pooled serum from control eugonadal subjects (2A, before acyline dose, baseline) and pools of all time-points after single oral dose of T at 200 mg (2B, T200) and 800 mg (2C, T800).
Figure 2B:
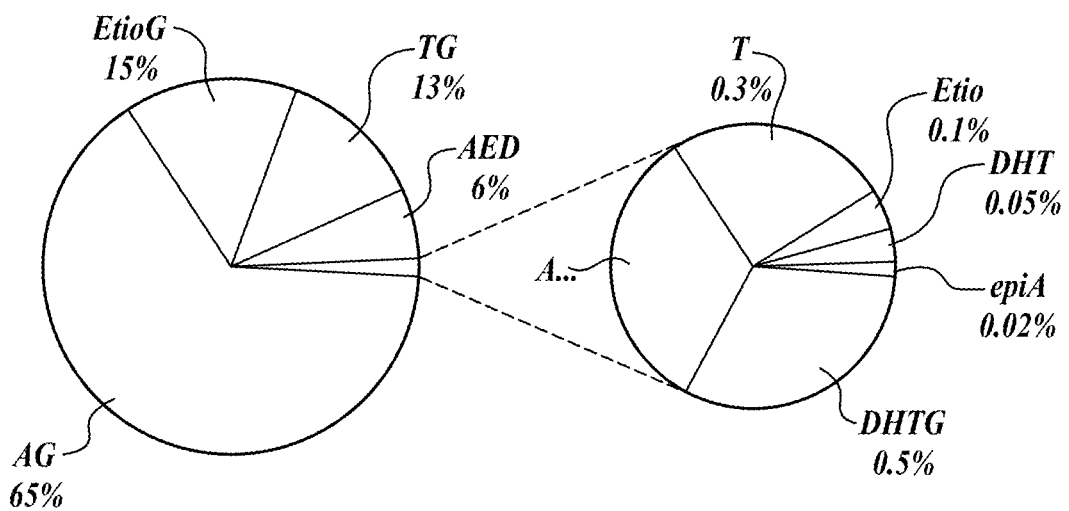
Figures 2C, 2D:
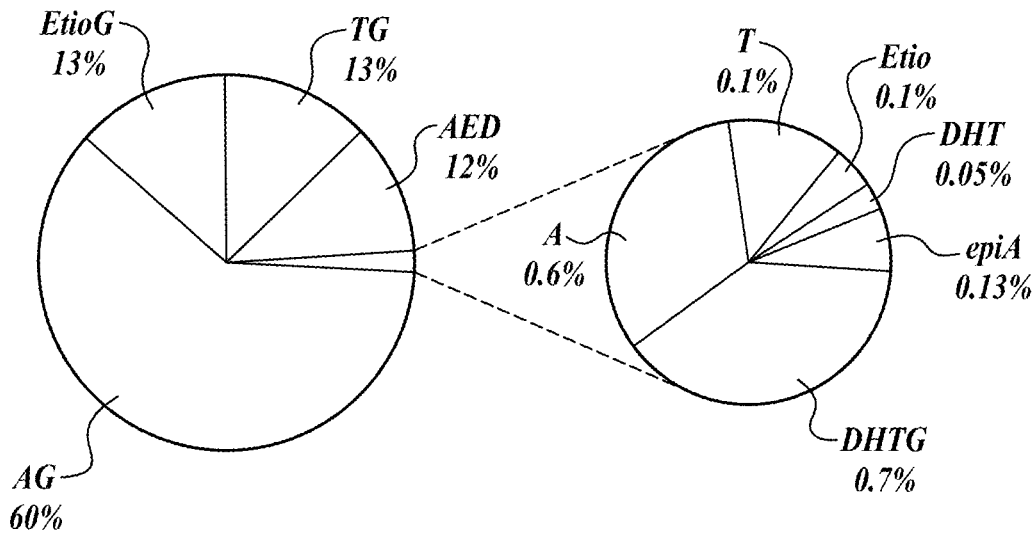

The relative concentrations of circulating T metabolites in eugonadal men (i.e., baseline levels prior to the induction of hypogonadism) is depicted in (FIG. 2A, upper panel). As expected, glucuronides were observed as the major circulating T metabolites; however, the relative predominance of AG over TG was surprising. When absolute levels of individual metabolites were compared at baseline and after dosing with 200 or 800 mg of oral T (T200 and T800) in the hypogonadal state (FIGS. 2B and 2C), TG was observed to be significantly higher as compared to baseline by 78 and 277-fold at T200 and T800, respectively. When compared to baseline, absolute levels of etiocholanolone glucuronide (EtioG), AG and DHT-glucuronide (DHTG) were 13, 9.5, and 7.5-fold at T200 vs. 39.5, 29.7, and 40.6-fold higher at T800 doses. Similarly, the absolute levels of unconjugated metabolites (AED, A, Etio and DHT) were 2.3, 1.2, 0.8 and 0.6-fold (T200) and 14.9, 5.5, 3.5 and 2.2-fold (T800) higher than that of baseline eugonadal state.

The average serum T AUC0-24 h was 81.6 nmol/L*h at T200 (FIG. 3 and Table 1). However, the major fraction of the oral T dose (T200) was present as its glucuronide metabolites in the serum with average $AUC_{0-24\ h}$ of 12,111 (AG), 2160 (EtioG) and 857.2 (TG) nmol/L-h (FIGS. 3 and 4). The average serum $AUC_{0-24\ h}$ of the un-conjugated metabolites were 26.5 (DHT), 373.7 (AED), 96.8 (A) and 11.2 (Etio) nmol/L-h. At T800 the $AUC_{0-24\ h}$ for T, TG, DHT, AED, A, AG, Etio, and EtioG were 2.1, 16.5, 3.3, 4.2, 12.6, 5.4, 8.2, and 6.9-fold, respectively, higher than that observed with T200, respectively (FIG. 4). 6β-0H-T was only detectable in few samples. Interestingly, multiple peaking phenomenon or humps in the serum concentration-time profile was observed in the individual subject data. $T_{max}$, $C_{max}$, and $t_{1/2}$ values derived from serum concentration-time profiles of T and all detected metabolites are presented in Table 1. Interestingly, the dose-normalized $AUC_{0-24\ h}$ data indicate that changing dose from 200 to 800 mg results in substantial increase in TG/T ratio by 9.3-fold. In contrast, $AUC_{0-24\,h}$ ratios (T200 vs. T800) were below 1 (AG/A and EtioG/A) or moderately increased (2-3 fold) (DHT/T, AED/T, A/AED, and Etio/AED).

Figure 5A:
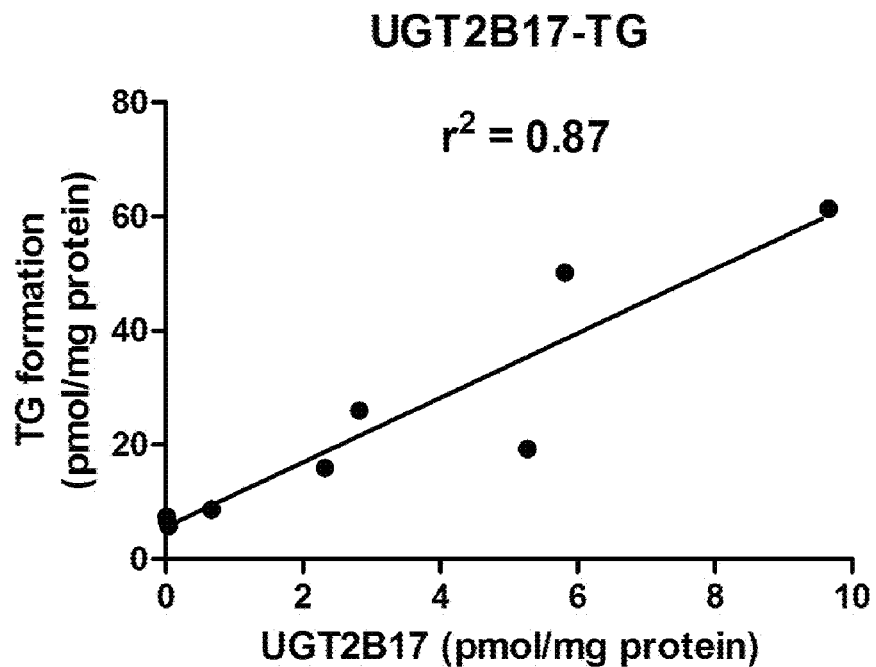
FIGS. 5A-5I demonstrate in vitro glucuronidation of T, A, and Etio using human liver microsomes (HLM) and recombinant human UGT2B enzymes.
Figure 5B:
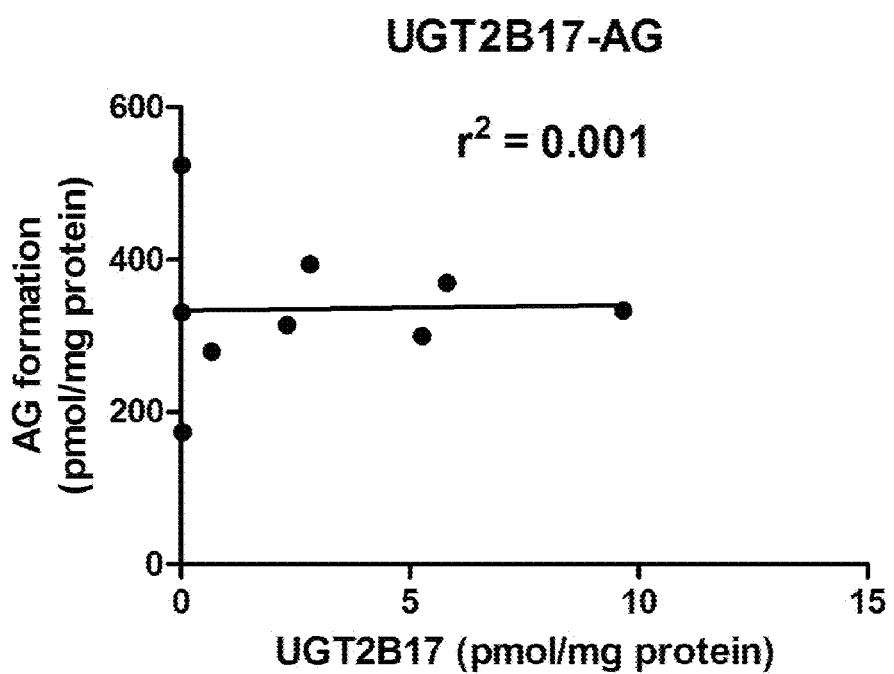
Figure 5C:
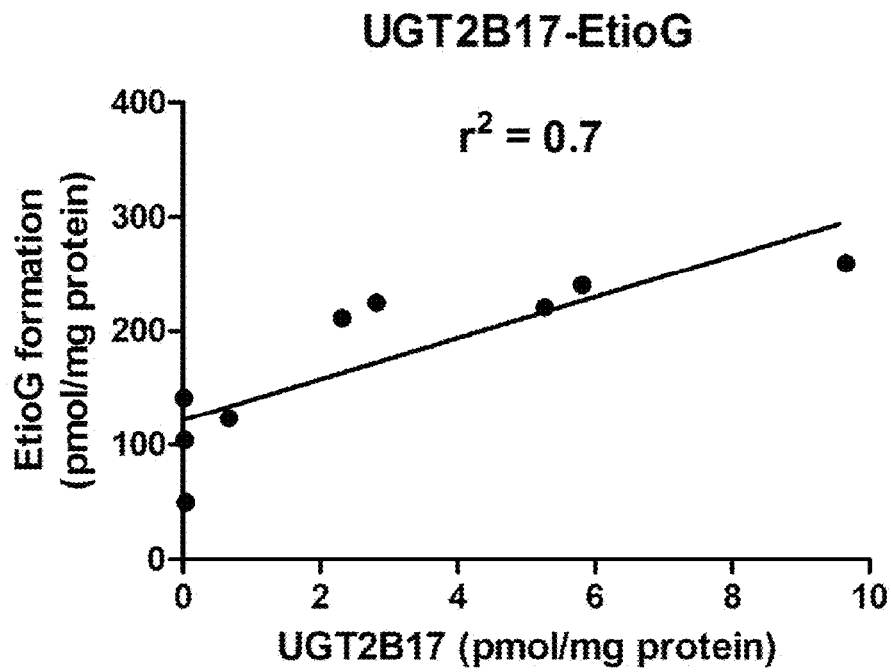
Figure 5D:
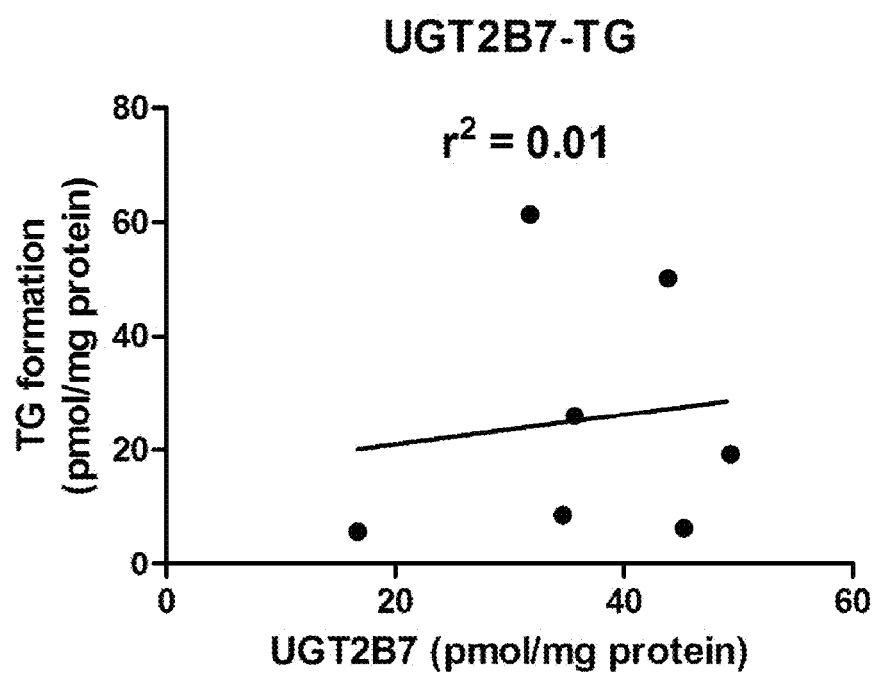
Figure 5E:
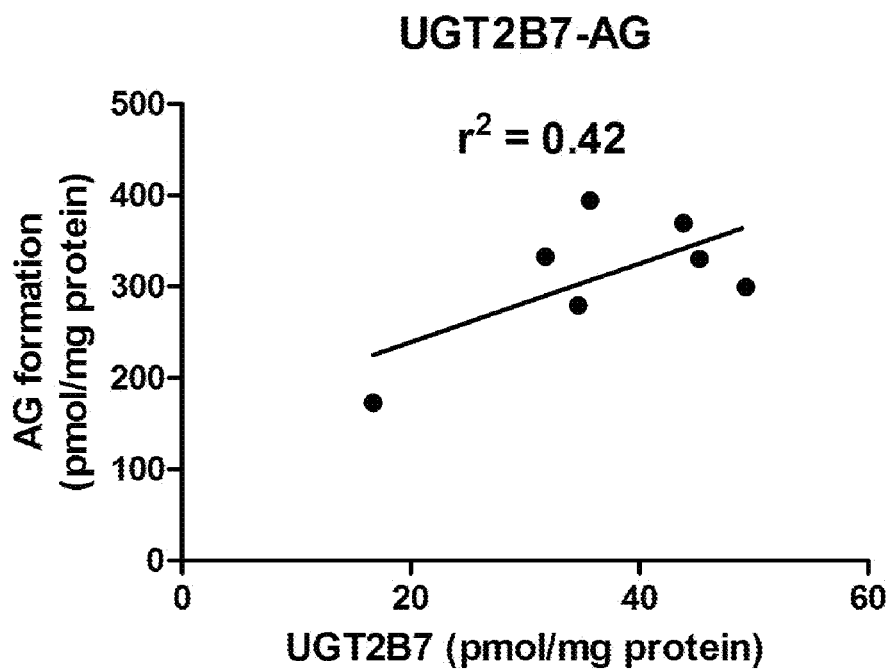

(FIG. 5A). These results were consistent with the recombinant UGT data. AG formation is primarily mediated by UGT2B7 as confirmed by recombinant UGT and HLM data.

TABLE 1

Pharmacokinetic parameters of testosterone and its metabolites after oral dose of testosterone at 200 and 800 mg with and without dutasteride

| PK Parameters | Dose group | T | TG | DHT | AED | A | AG | Etio | EtioG |
|---|---|---|---|---|---|---|---|---|---|
| $t^{1/2}$ (h) | T200 | 12.0 | 4.4 | 17.6 | 12.7 | 15.6 | 4.9 | 19.0 | 5.2 |
| | T200 + D | 7.0 | 4.3 | 24.0 | 8.3 | 15.2 | 4.5 | 11.3 | 10.5 |
| | T800 | 5.3 | 3.6 | 6.9 | 6.8 | 8.2 | 4.5 | 10.7 | 7.8 |
| | T800 + D | 5.7 | 2.7 | 17.9 | 5.2 | 16.1 | 6.3 | 6.4 | 9.9 |
| Tmax (h) | T200 | 4 | 2 | 2 | 2 | 2 | 6 | 2 | 2 |
| | T200 + D | 4 | 4 | 4 | 2 | 2 | 4 | 2 | 4 |
| | T800 | 4 | 1 | 2 | 1 | 2 | 4 | 1 | 1 |
| | T800 + D | 2 | 2 | 4 | 2 | 2 | 4 | 2 | 2 |
| Cmax (nmol/L) | T200 | 6.0 | 149.3 | 2.0 | 66.3 | 11.0 | 1404.1 | 1.2 | 266.9 |
| | T200 + D | 8.8 | 64.5 | 0.8 | 199.7 | 5.6 | 372.2 | 3.5 | 414.3 |
| | T800 | 16.8 | 1937.3 | 8.4 | 280.5 | 168.5 | 5649.1 | 12.4 | 1129.4 |
| | T800 + D | 33.0 | 1174.1 | 1.8 | 2301.9 | 13.0 | 1346.5 | 33.9 | 2096.4 |
| AUC 0-24 h (nmol/L*h) | T200 | 81.6 | 857.2 | 26.5 | 373.7 | 96.8 | 12110.8 | 11.2 | 2160.4 |
| | T200 + D | 84.7 | 373.4 | 9.6 | 1634.9 | 68.5 | 2582.7 | 24.4 | 3277.3 |
| | T800 | 168.9 | 14163.0 | 87.4 | 1551.8 | 1218.9 | 65427.8 | 91.7 | 14981.5 |
| | T800 + D | 293.8 | 8589.7 | 26.6 | 10844.4 | 161.5 | 14867.7 | 220.2 | 27091.7 |
| V/F_obs (L) | T200 | 110034 | — | — | — | — | — | — | — |
| | T200 + D | 72890 | — | — | — | — | — | — | — |
| | T800 | 118392 | — | — | — | — | — | — | — |
| | T800 + D | 72597 | — | — | — | — | — | — | — |
| Cl/F_obs (L/h) | T200 | 6351 | — | — | — | — | — | — | — |
| | T200 + D | 7202 | — | — | — | — | — | — | — |
| | T800 | 15528 | — | — | — | — | — | — | — |
| | T800 + D | 8831 | — | — | — | — | — | — | — |

T = Testosterone,
TG = Testosterone glucuronide,
DHT = 5α-Dihydrotestosterone,
AED = Androstenedione,
A = Androsterone,
AG = Androsterone glucuronide,
Etio = Etiocholanolone,
EtioG = Etiocholanolone glucuronide The pooled serum T levels were 1.4 and 2.4-fold higher after dutasteride co-administration at T200 and T800, respectively as compared to T alone. The average $AUC_{0-24\,h}$ was 3277, 2583, and 373.4 nmol/L*h for EtioG, AG, and TG, respectively after 200 mg T with dutasteride (T200+D), which were 151, 21, and 43% with respect to T alone. The average AUC0-24 h at 800 mg T with dutasteride (T800+D) were 180, 22, and 60% as compared to T alone (FIG. 3 and Table 1). The average $AUC_{0-24\,h}$ for DHT with dutasteride was 64% and 70% lower in T-treated samples (T200 and T800, respectively) as compared to T alone. The circulating A level was 30% (T200+D) and 87% (T800+D) lower in dutasteride treated samples as compared to T alone. On the other hand, circulating levels for AED and Etio were 5.7 and 2.3-fold higher in T200+D and T800+D as compared to T alone.

Figure 3A:
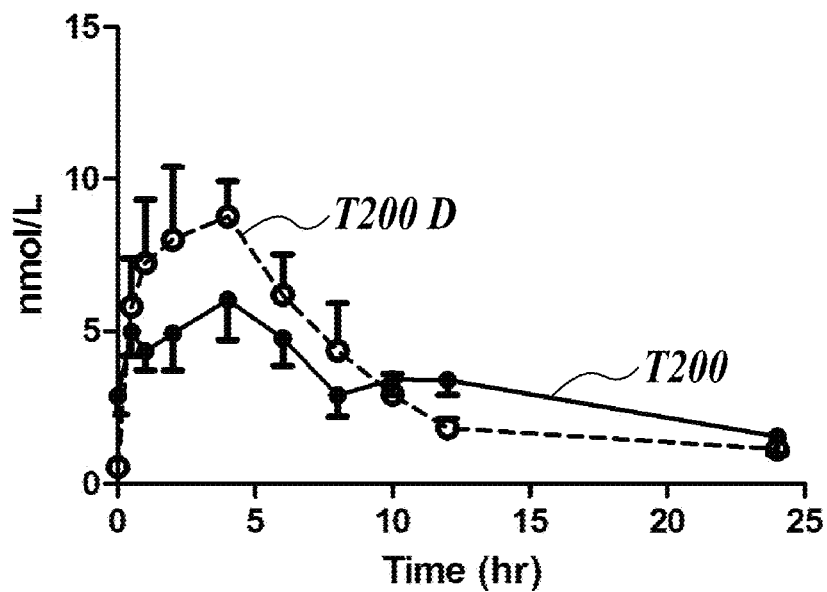
FIGS. 3A-3C show the effect of oral dutasteride on oral T metabolism in vivo and in vitro.
Figure 3A:
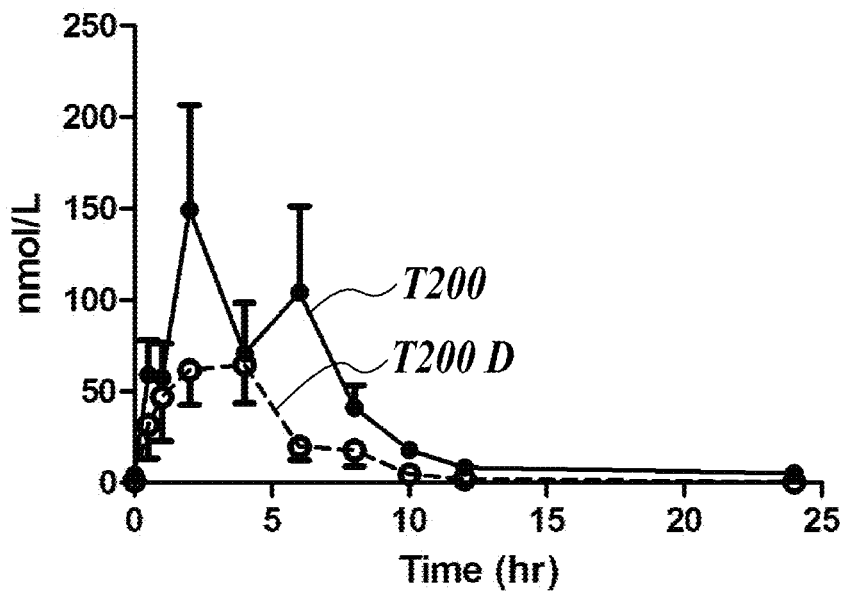
Figure 3A:
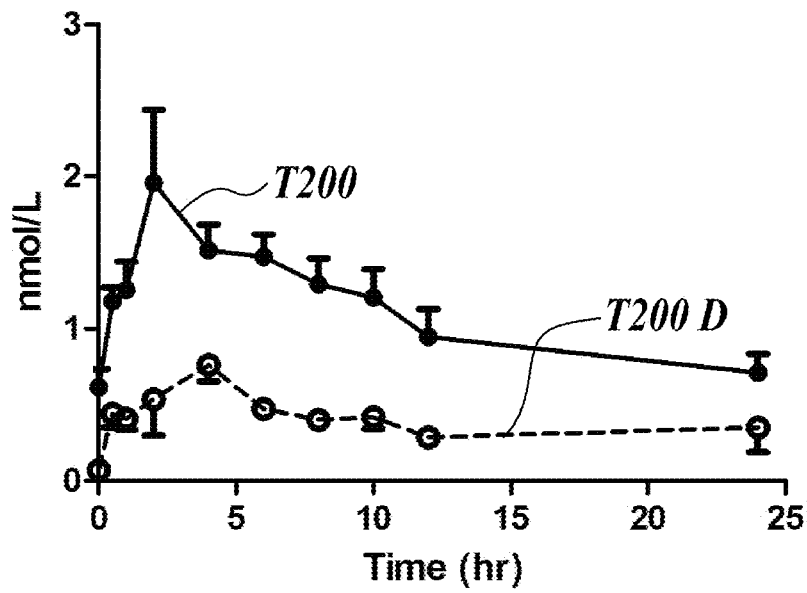
Figure 3A:
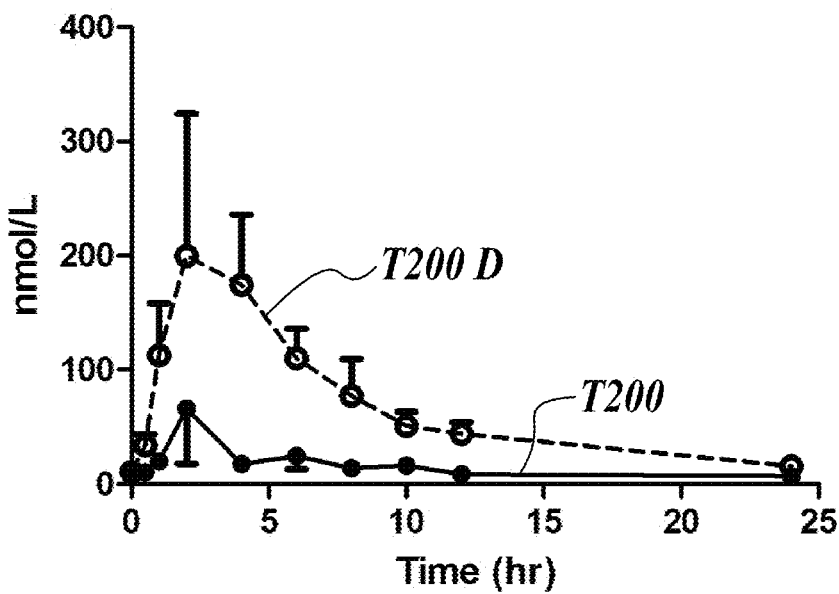
Figure 3A:
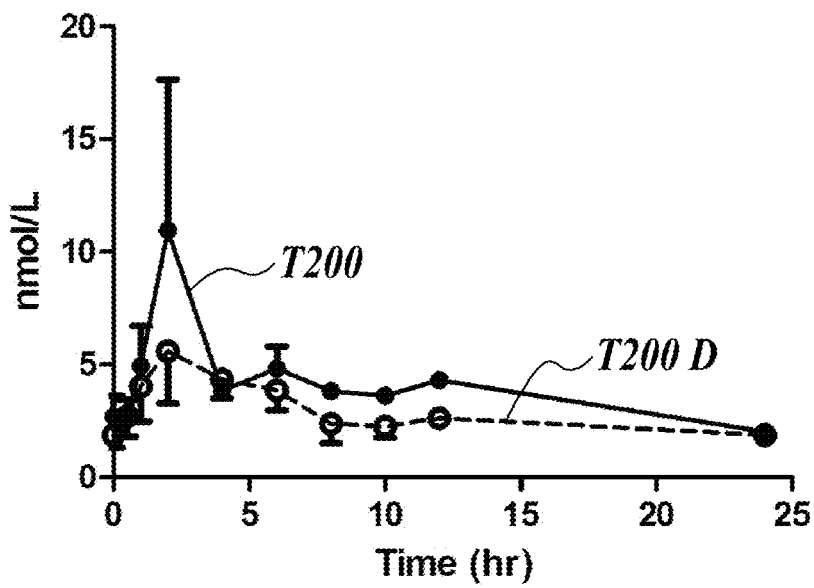
Figure 3A:
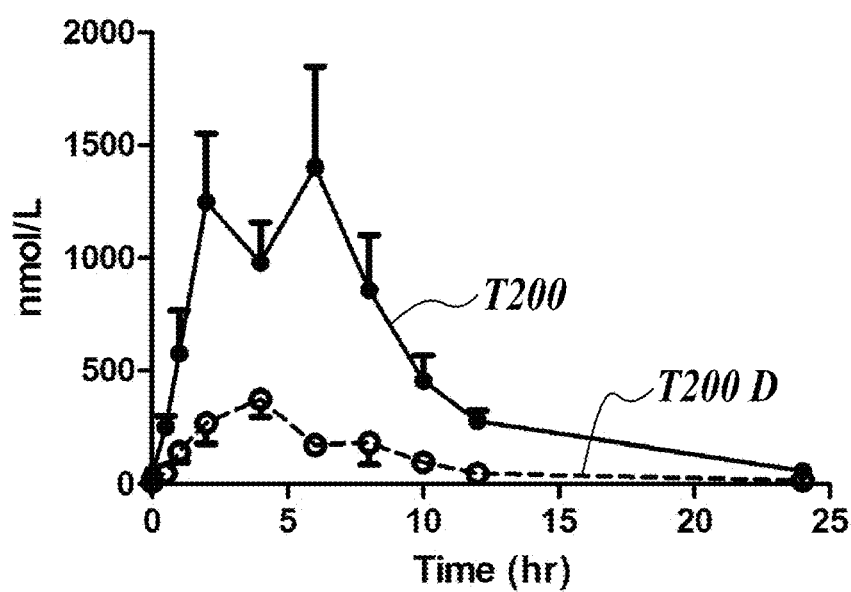
Figure 3A:
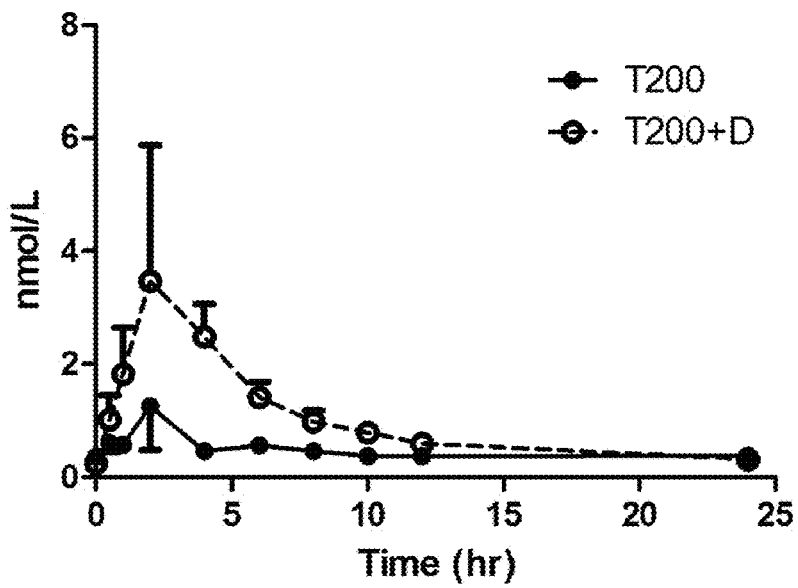
Figure 3A:
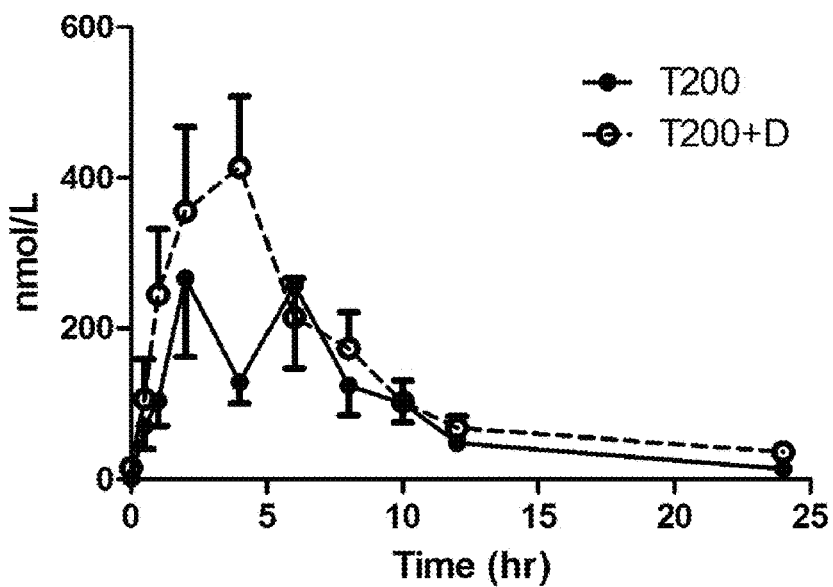
Figure 3B:
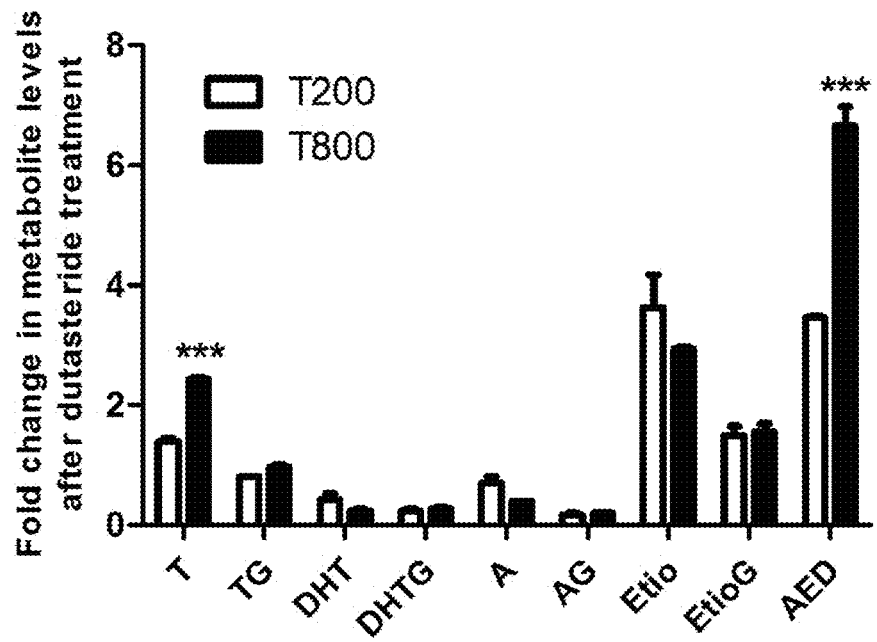
Figure 3C:
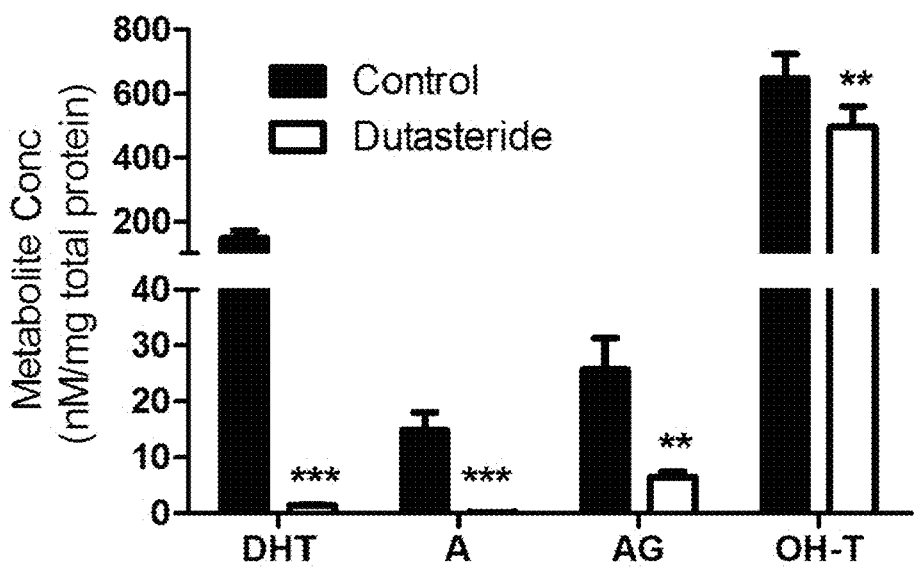

Consistent with the in vivo data, co-treatment of dutasteride with T resulted in complete inhibition of 5-AR type 1 and 2 mediated metabolism of T in human hepatocyte. This resulted in significant decreases in DHT, A, AG and 6β-OH-T formation (FIG. 3C, p<0.01). No significant changes were observed in the levels of TG and AED (data not shown).

In human liver microsomes (HLM), T is primarily glucuronidated by UGT2B17 with minor contribution from UGT2B15 (FIGS. 5A-5I). For example, there was a good correlation between TG formation and UGT2B17 protein abundance in human liver microsomes (HLM) ($r^2=0.87$)

Figure 5F:
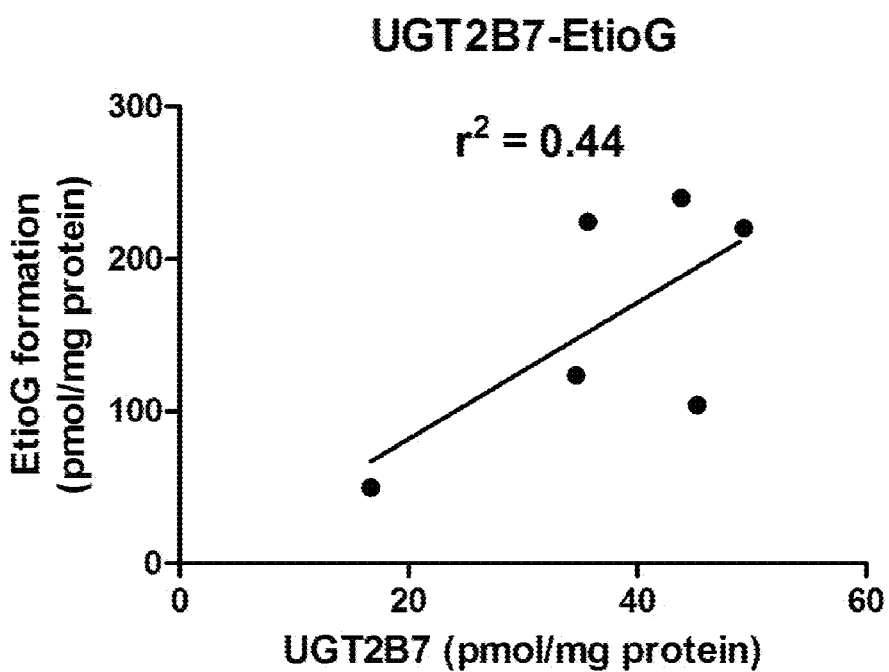
Figure 5G:
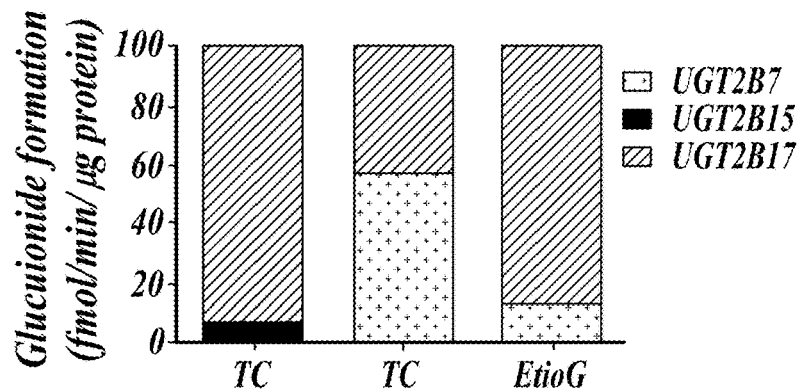
Figure 5H:
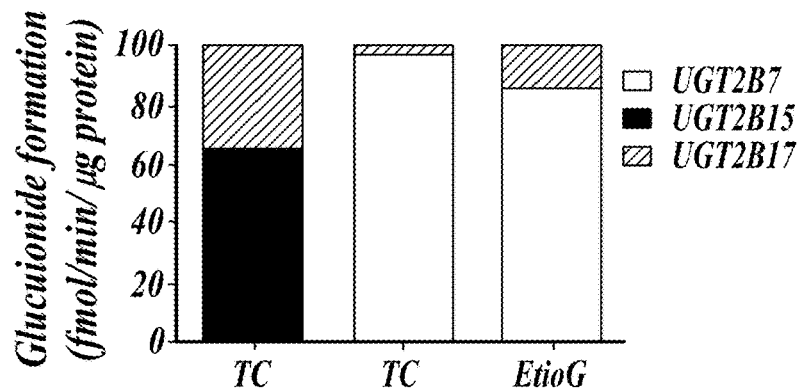
Figure 5I:
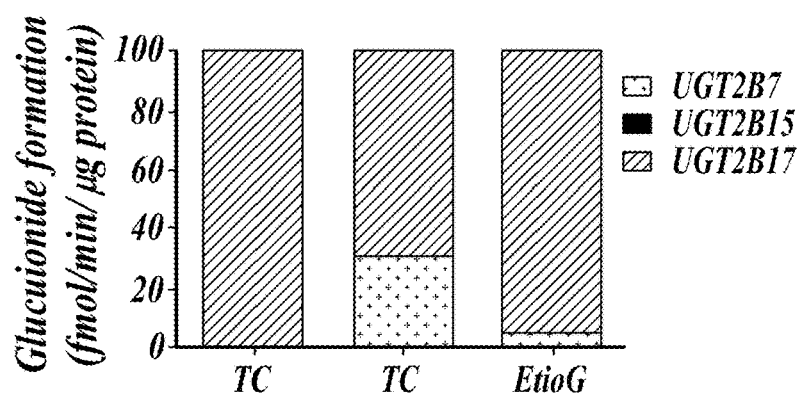

Etio is metabolized by both UGT2B17 ($r^2=0.7$, FIG. 5C) and UGT2B7 ($r^2=0.44$, FIG. 5F). Scaling these data by using absolute UGT2B abundance in the intestine and the liver predicts that UGT2B17 is the major contributor for the intestinal glucuronidation of T (100%), Etio (90%) and A (70%), whereas UGT2B7 is the major contributor for hepatic glucuronidation of A (100%) and Etio (85%).

Discussion

Approximately 2-5% men are affected by hypogonadism, which requires TRT. Because of high-first pass metabolism, only non-oral T formulations are available in the US, and these formulations are frequently associated with poor patient compliance and variable response. In order to develop strategies to ensure optimum T bioavailability, it is important to characterize mechanisms that affect first-pass T metabolism. As described herein, it was observed that the metabolism of T differs between eugonadal men and those same men treated with oral T after induction of hypogonadism. Particularly, distinctly high AG, TG, and EtioG concentrations in T-treated vs. untreated samples indicate that glucuronidation is the major mechanism of T first-pass elimination. Of particular note, the inventors observed that, contrary to the prevailing thinking, glucuronidation of oral T to AG appeared to be more prevalent than formation of TG. While the clearance of TG and AG may differ (depending on differential renal clearance) and therefore individual contribution of each pathway (fm) cannot be calculated from the circulating metabolite concentration data, this finding suggests that "back-formation" of AED via 17β-HSD2 is the primary route of metabolism of oral T. Interestingly, relative proportions of AG and EtioG to all metabolites (FIGS. 2A-2D) were marginally different from their proportion at baseline; however proportion of TG (baseline vs. treated) to all metabolites differ significantly. Although genotype data were not available to us in this study, high interindividual variability in TG PK profiles was consistent with polymorphic nature of UGT2B17.

Although AED can also be biosynthesized from dehydroepiandrosterone (DHEA) by 3α-HSD, T to AED via 17β-HSD2 was observed as the major T metabolic pathway, which subsequently metabolized to the major metabolites, AG and EtioG. These data are corroborated by Bhasin et al., which showed the association of aldo-keto reductase 1C3 (AKR1C3/17β-HSD5) polymorphism (rs12529) with variable T circulating levels in men (Bhasin, S. et al. Contributors to the substantial variation in on-treatment testosterone levels in men receiving transdermal testosterone gels in randomized trials. *Andrology* 6, 151-7 (2018)). High levels of AED and its metabolites with oral T are presumably due to interaction of T with 17β-HSDs and AED with 5α/β-reductase (5-AR/5-BR) in the gastrointestinal tract and liver during the first-pass. High in vitro formation of AED (46%) from T using primary human hepatocyte was confirmed, but it was marginally higher than TG levels (42%). Because 17β-HSDs are also expressed in the intestine, T to AED formation can occur in the enterocyte. Thus inhibition of 17β-HSD2 in the intestine and the liver can significantly increase T circulating levels, and could be used as a potential therapeutic target for augmenting the effect of oral TRT. This is important as the development of 17β-HSDs inhibitors is in the early stage for treatment of osteoporosis (17β-HSD1/2) and prostate cancer (17β-HSD3/5).

Although relative to AED, TG formation was observed to be a minor pathway in overall T metabolism, it is noteworthy that T to TG conversion is mediated by a highly variable enzyme, UGT2B17. Because ~50% population has a very low expression (non-detectable in the liver, T-glucuronidation will be important only in the high UGT2B17 expressers (e.g., in 10% population). This is supported with controversial association of UGT2B17 with T-related pathophysiological conditions, prostate cancer. That is, while some studies support association of UGT2B17 gene deletion with prostate cancer, a recent large study failed to confirm the same, perhaps due to high variability in UGT2B17. Particularly, that UGT2B17 is associated with single nucleotide polymorphism (rs7436962, rs9996186, rs28374627 and rs4860305), age and gender besides gene deletion has been demonstrated.

Here, a 4-fold increase in dose (200 to 800 mg) only resulted in 2-fold increase in circulating T concentrations. For the first time the inventors demonstrated that T metabolism to TG and AED increases more than proportionally with increasing dose. Higher TG formation after 800 mg dose could be because of the cumulative effect of a) the dose-limiting T solubility resulting in longer gastro intestinal (GI) retention of T and b) higher UGT2B17 abundance in lower part of GI tract (unpublished data). Interestingly, AG and EtioG formation seems to saturate at the higher dose (800 mg). Because metabolite ratios are used to create individual passports, these findings should be considered when analyzing doping test results.

Figure 4A:
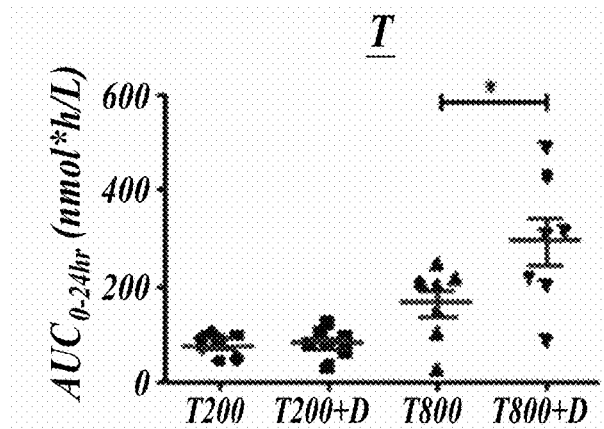
FIG. 4A shows the $AUC_{0-24\ h}$ of T and its primary and secondary metabolites in individual subjects after single oral dose of T at T200 and T800 with and without dutasteride co-administration. Dots indicate individual data, horizontal line represents mean and error bars indicate SE.
Figure 4A:
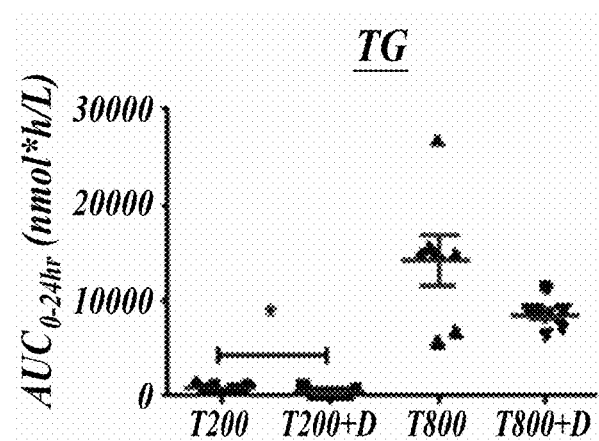
Figure 4A:
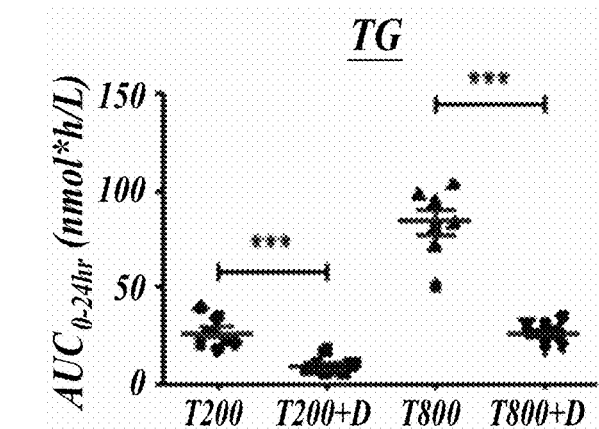
Figure 4A:
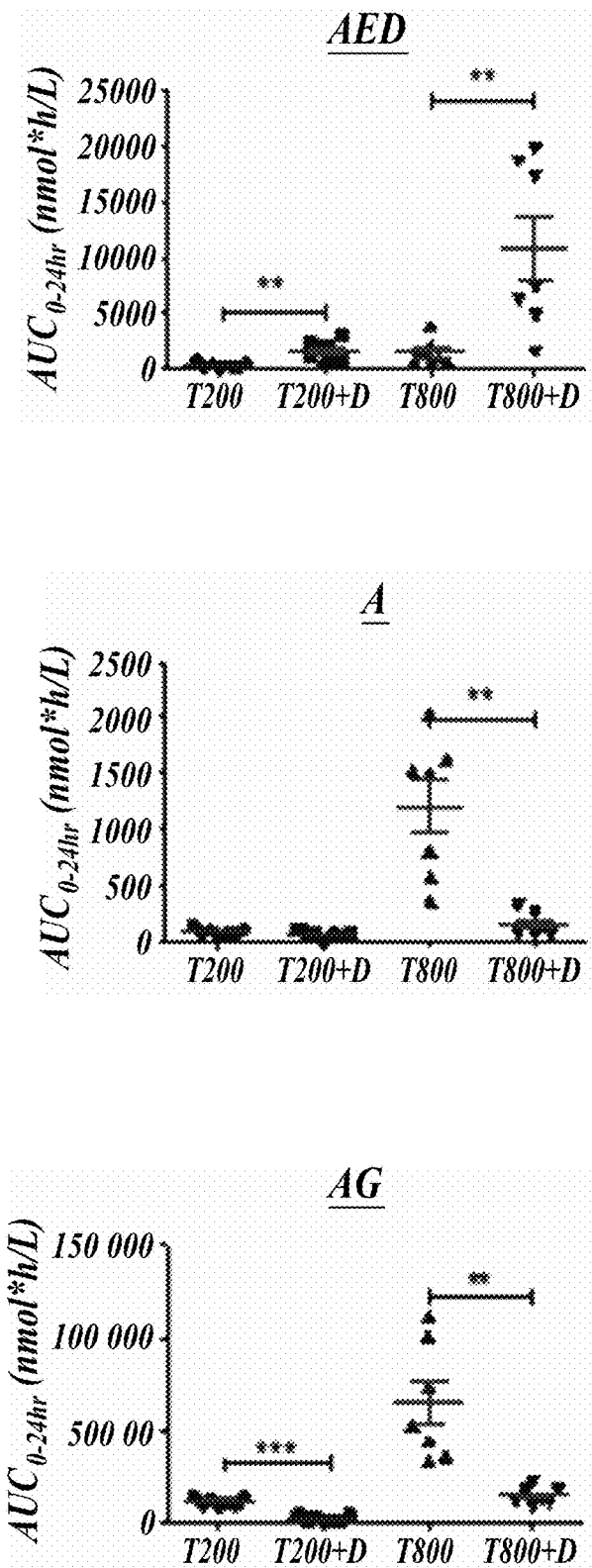
Figure 4A:
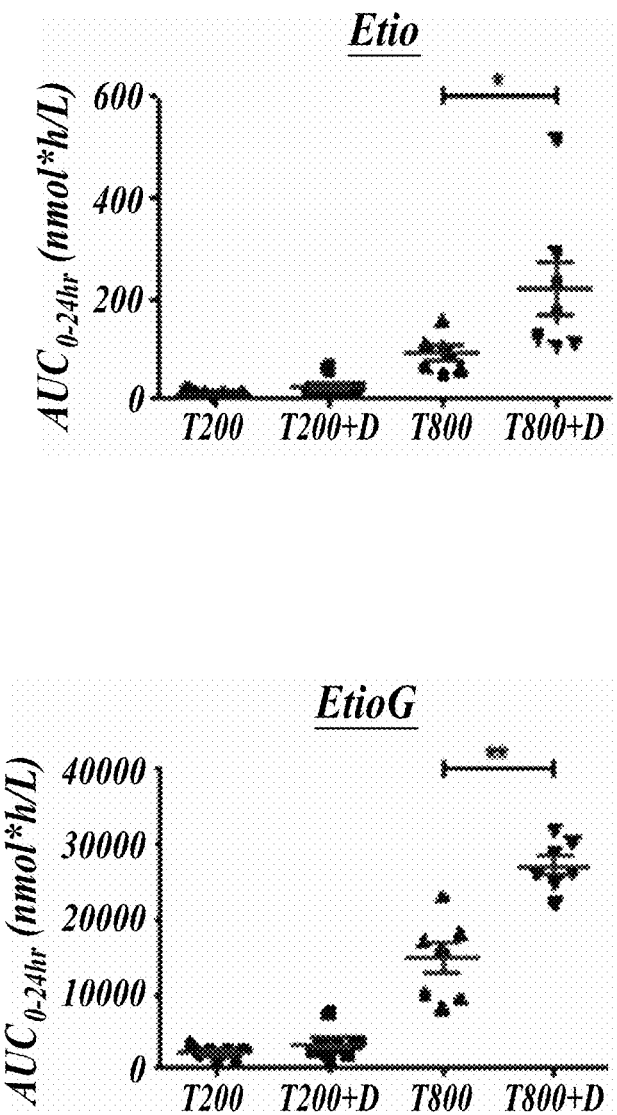
Figure 4B:
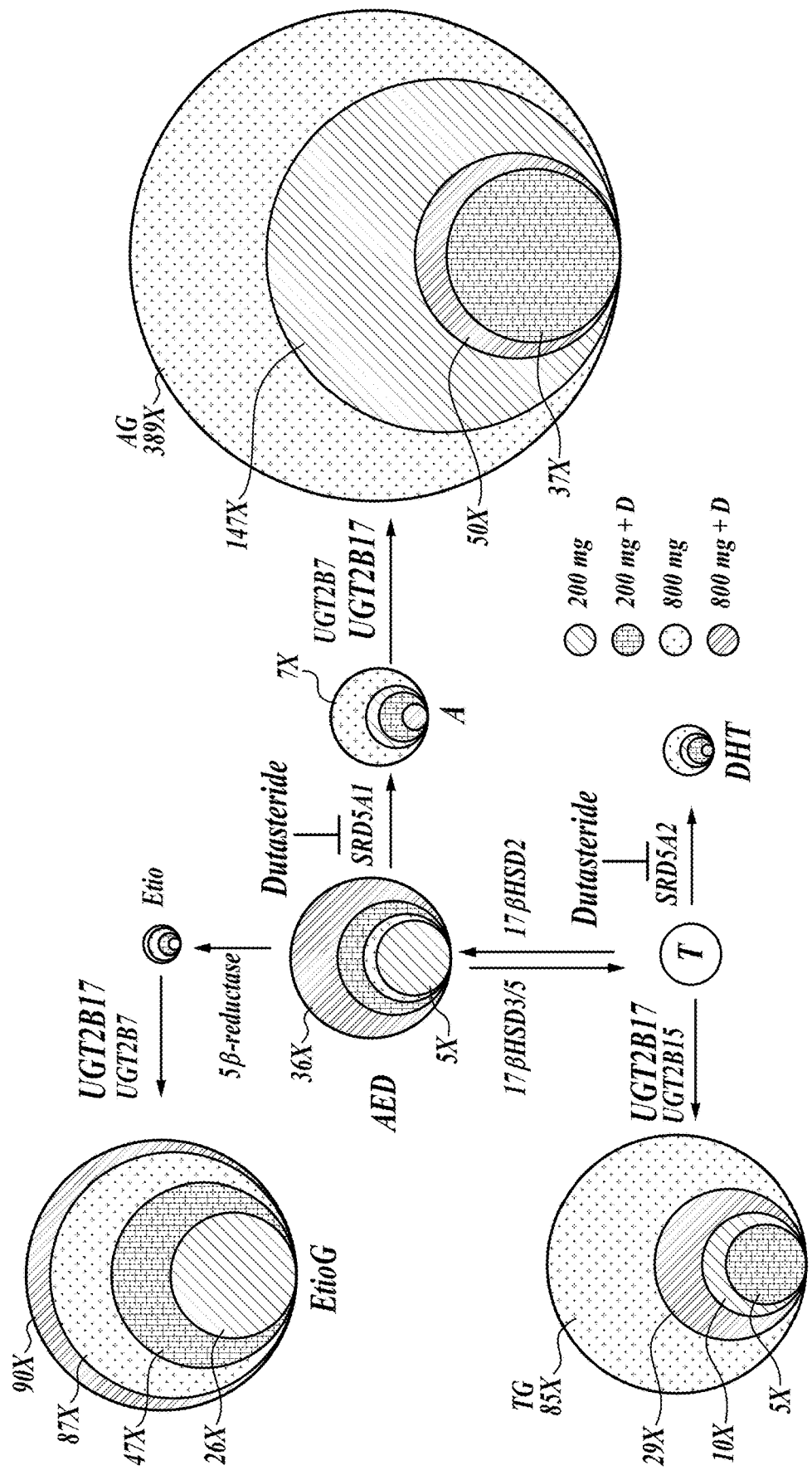
FIG. 4B shows relative quantitative representation of mean AUC0-24 h of T, and its primary and secondary metabolites after single oral dose at T200 and T800 with and without dutasteride co-administration. Metabolic scheme and enzymes involved in T metabolism are shown. Size of the circle and number (nx) indicate relative mean $AUC_{0-24\ h}$ of individual metabolites as compared to T in respective studies. Glucuronides are the major circulating metabolites of T.

Dutasteride co-administration resulted 2-fold higher serum T concentration after 800 mg oral T dose. This increase in serum T levels are due to dual inhibition of 5-AR type 1 and 2, and would likely not be evident with a specific inhibitor for Type-2 5-AR e.g., finasteride. Interestingly, there was no significant increase in serum T levels at 200 mg T dose with dutasteride perhaps due to low levels of AED in T200 as compared to T800 which seemed necessary to drive the back-conversion (FIG. 4A). A moderate reduction in TG levels was observed with dutasteride at 200 and 800 mg T. However, inhibition of UGT2B17 or induction of 17-HSD2 do not explain these observations as indicated by in vitro data.

The above described study has several limitations, including, a small number of subjects, and the non-availability of urine samples and DNA for genotyping. The sulfate conjugates could not be detected in this study due to analytical challenges of these low level metabolites or perhaps due to rapid elimination of sulfates in urine. Nevertheless, the data presented herein are novel with respect to levels of circulating glucuronides, non-linear PK and effect of dutasteride on T metabolite profiles. In particular, the relative prominence of the AG vs. the TG pathway for the metabolism of oral T was unexpected and may be useful in the development of novel formulation strategies of oral T. In addition, the non-linear PK of oral T observed in this study should be taken into consideration while developing anti-doping strategies. Multiple peaking phenomenon in the PK profiles suggests a potential role of microbiome in deconjugation of glucuronides, indicating another potential reasons of inter-individual variability. This is consistent with data that revealed that transfer of cecal contents from male mice to female mice was associated with increased circulating T in female mice (Markle, J. G. et al. Sex differences in the gut microbiome drive hormone-dependent regulation of autoimmunity. *Science* 339, 1084-8 (2013)).

B. Effect of Oral Testosterone on Steroid Metabolome and Discovery of a Serum Biomarker of UGT2B17 Inter-Individual Variability UGT2B17 is a highly variable enzyme, which is responsible for metabolism of drugs and androgens. Because UGT2B17 variability could not be explained by genetic polymorphism alone, it is important to identify a circulating biomarker of UGT2B17 activity for stratification of patients receiving UGT2B17 substrates such as vorinostat, exemestane and testosterone (T). The objective was to identify a potential serum biomarker of UGT2B17 by (i) accomplishing metabolomics analysis after oral T dosing, and (ii) performing an in vitro mechanistic study to compare correlation of steroid glucuronides vs. UGT2B17 protein abundance in T-treated human hepatocytes.

Methods.

A targeted metabolomics study was performed on previously collected samples from an oral T pharmacokinetics (PK) study (800 mg). T and its primary and secondary metabolites in serum were quantified, and PK data of these steroids were analyzed using the non-compartmental method. UGT2B reaction phenotyping was also performed to identify whether UGT2B7, UGT2B15, and/or UGT2B17 metabolize T, androsterone (A) and etiocholanolone (Etio) in recombinant UGT2Bs and human liver microsomes characterized for UGT2B abundance. Additionally, T-metabolism study was also performed in human hepatocytes for 1 h. The media and cell pellets were collected for subsequent metabolomics and proteomics analyses, respectively. Effect of dutasteride treatment on androgen metabolome was also investigated, both in vivo and in vitro. A UGT2B17 biomarker was identified based on correlation of TG or TG/AG vs. UGT2B17 abundance in human hepatocytes and the approach was applied to predict in vivo UGT2B17 variability.

Results.

With 800 mg dose, AUC0-24 h of T-glucuronide (TG), androsterone glucuronide (AG), etiocholanolone glucuronide (EtioG) was 85, 389 and 87-fold higher in human serum as compared to T AUC0-24 h (nmol·h/L). Similarly, TG and AG were also detected in hepatocyte media, albeit TG levels were 3.7-fold lower than AG in the media. AG formation rate (i.e., AG/A) was constant in all the four hepatocyte donors, whereas TG/T ratio was highly variable, which strongly correlates with UGT2B17 protein abundance ($r^2$=0.93). The correlation between TG and TG/AG remained strong when 5α-reductase was inhibited by dutasteride ($r^2$=0.90). Consistent to these findings, the superosomes and microsomes reaction phenotyping data also confirmed UGT2B17 as a selective T-glucuronidation enzyme, with limited AG and EtioG formation activity. This approach when applied to the in vivo data, confirmed high variability in TG/AG ratio consistent with UGT2B17 in vivo expression, which was also reflected by strong correlation ($r^2$=0.84) between serum TG and TG/AG was also observed.

Conclusion.

TG/AG ratio can be used as a serum biomarker of UGT2B17 variability because TG and AG formation is mediated by different UGTs. The approach demonstrated herein can be used in precision therapy of vorinostat, exemestane, and T. Further, the serum biomarker of UGT2B17 variability is useful in T doping control.

C. Precision Medicine Approach: Fractional Contribution of UGT2B15 and UGT2B17 in Testosterone Glucuronidation in Human Liver Microsomes and its Variability Testosterone has poor and variable oral bioavailability, thus leading to unreliable predictions of its oral pharmacokinetics. Testosterone glucuronidation is the major route of testosterone elimination, and UGT2B15 and UGT2B17 are considered the main enzymes responsible.

Figure 6A:
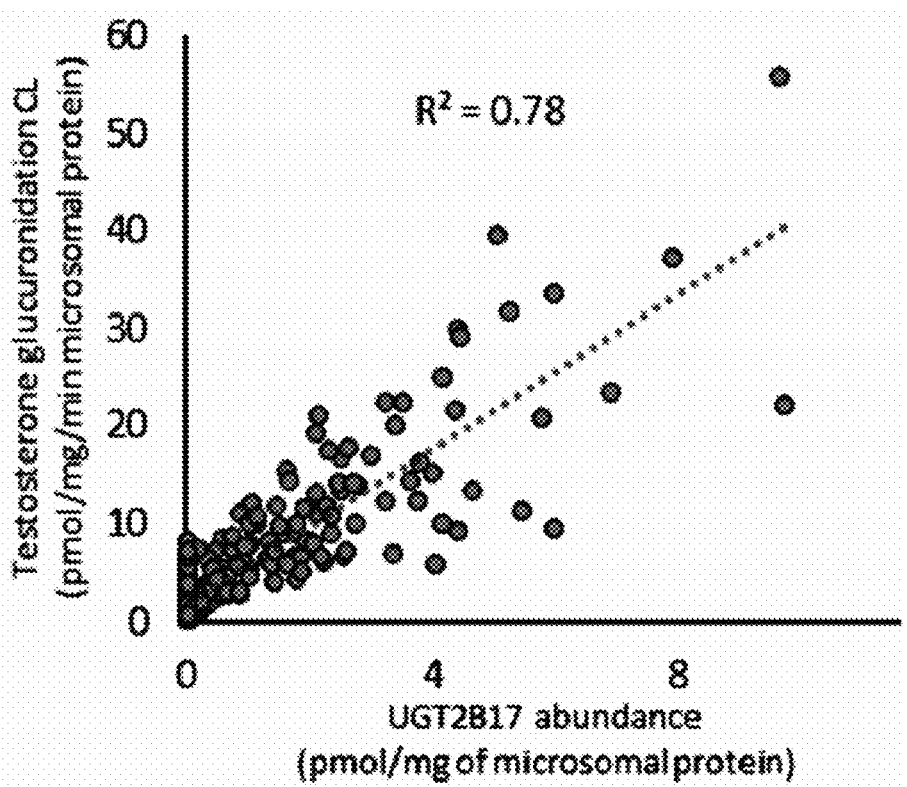
FIGS. 6A-6D demonstrate that testosterone glucuronide (TG) formation strongly correlates with the UGT2B17 abundance in human liver microsomes (6A). TG formation (6B), UGT2B17 protein abundance and mRNA expression are associated with its gene copy number variation, age (6C) and sex (6D). However, a significant proportion (~74%) of variability in UGT2B17 is unexplained.
Figure 6B:
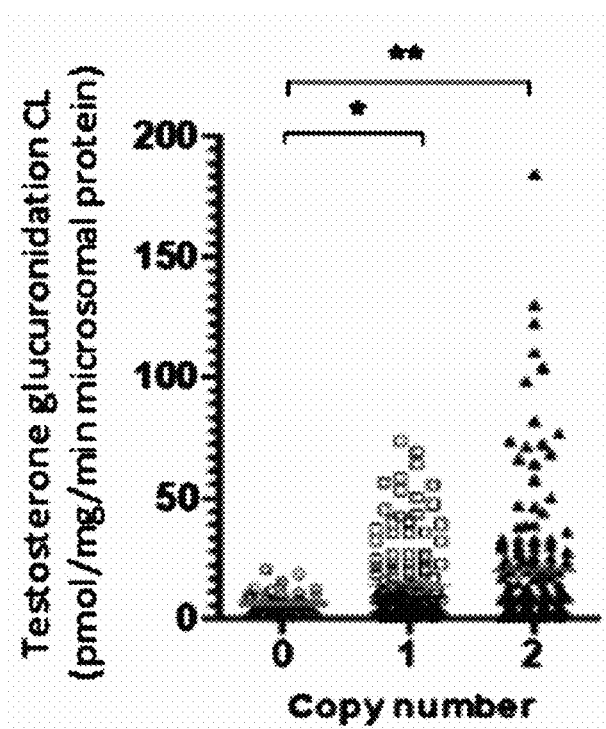
Figure 6C:
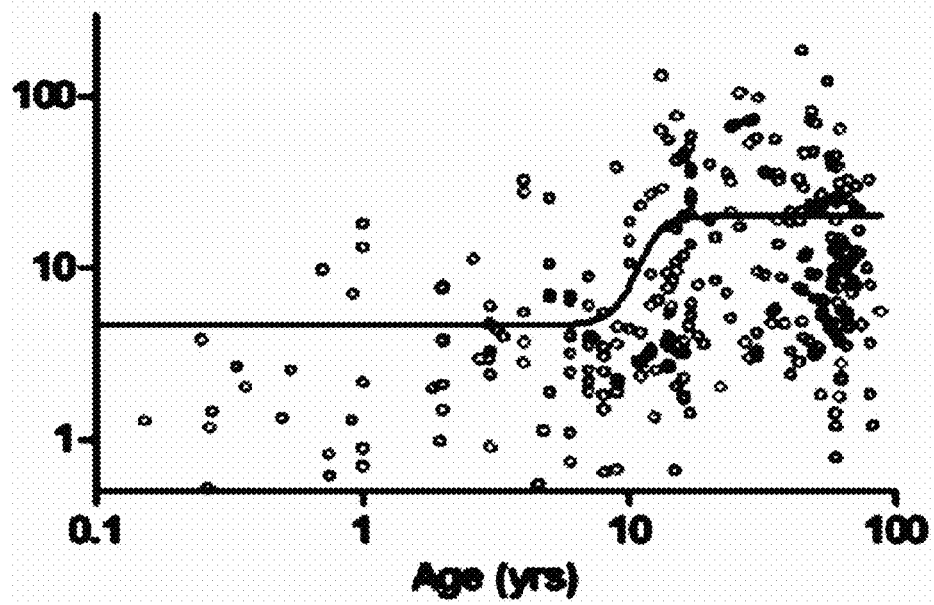
Figure 6D:
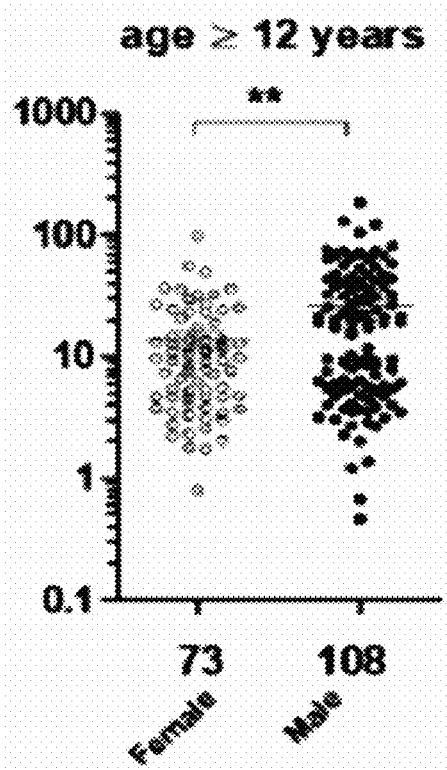
Figure 7:
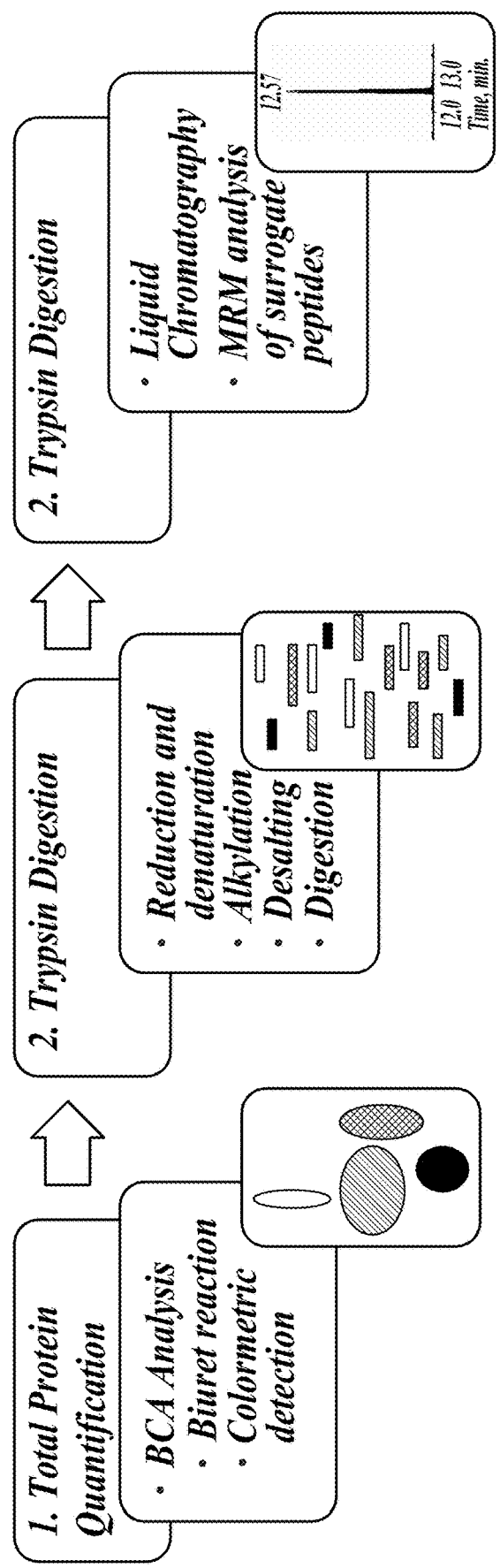
FIG. 7 is an overview of validated proteomic assay protocol used for quantification for UGT2Bs in human tissues.

In particular, UGT2B17 exhibits gene deletion which has been associated with false negative anti-doping test results, increased risk of prostate cancer, and drug development failure. The inventors have shown that high variability has been observed with UGT2B17 with ontogenic and gender effects (FIGS. 6B and 6C).

In order to predict testosterone hepatic metabolism and its variability, the inventors estimated the fractional contributions of UGT2B15 and UGT2B17 in testosterone hepatic glucuronidation by performing in vitro activity and quantitative proteomic assays in human liver microsome (HLM) samples genotyped for UGT2B17 deletion.

The present disclosure addresses treating testosterone deficiency in men using a precision medicine approach. Based on analysis of human samples, the inventors have identified that a critical enzyme involved in testosterone urinary elimination is highly variable in men. The inventors then identified a specific testosterone metabolite as a biomarker in this special population of men using metabolomics, genomics, and proteomics approach. By inhibiting this enzyme, alone or in combination of testosterone, testosterone deficiency in men can be treated.

Methods.

Figure 8:
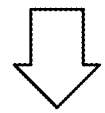
FIG. 8 is an overview of testosterone glucuronidation activity assay in human liver microsomes (HLM) isolate from individual human tissues.
Figure 8:
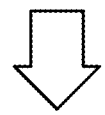
Figure 9B:
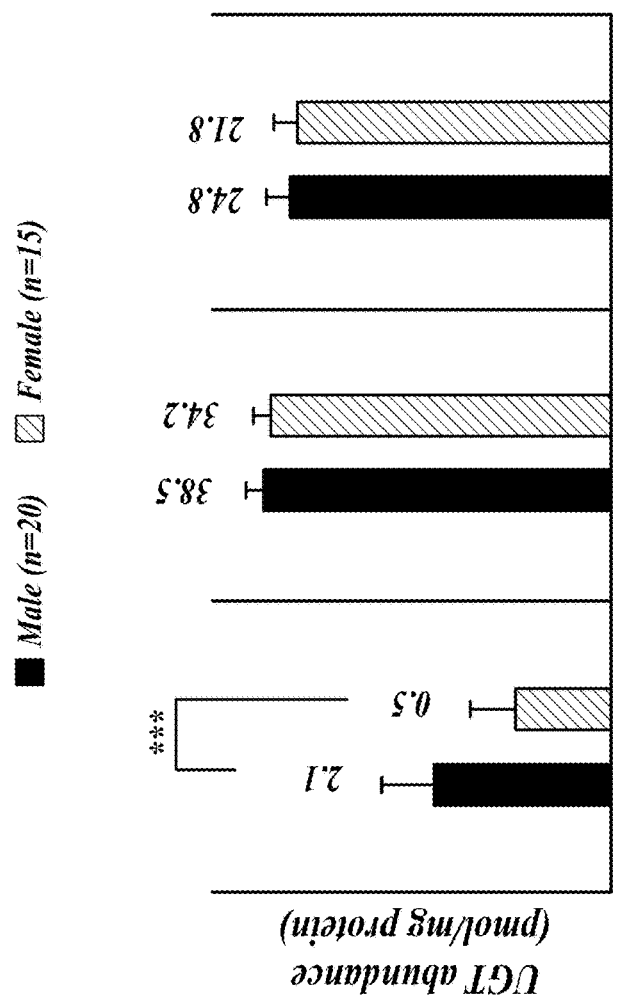
FIG. 9B demonstrates that UGT2B17 expression is higher in males vs. females but sex has no association with UGT2B7 or UGT2B15 abundance.
Figure 9A:
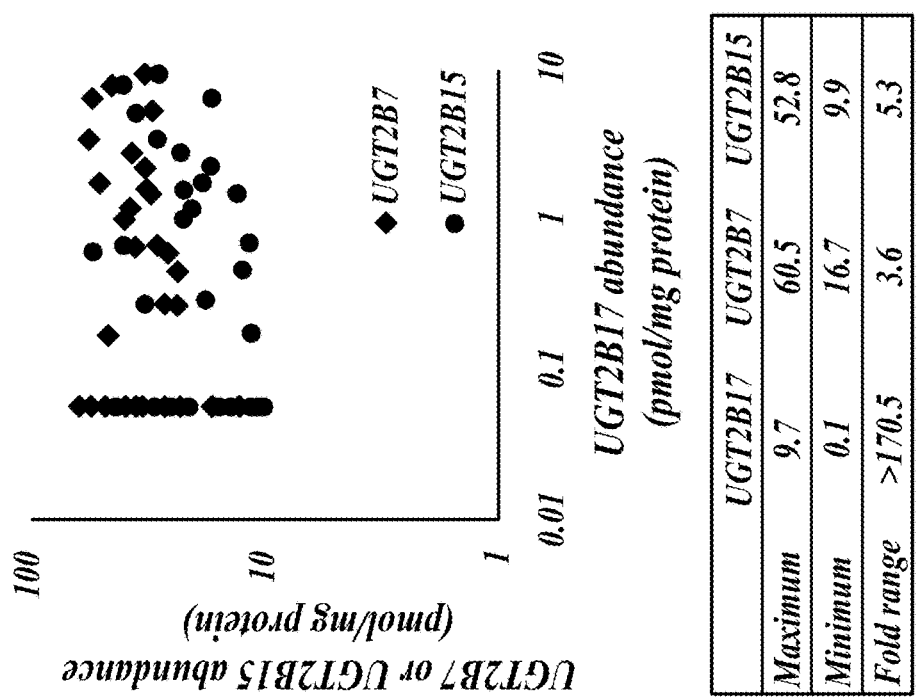
FIG. 9A shows that UGT2B7 and UGT2B15 are significantly less variable than UGT2B17.
Figure 10:
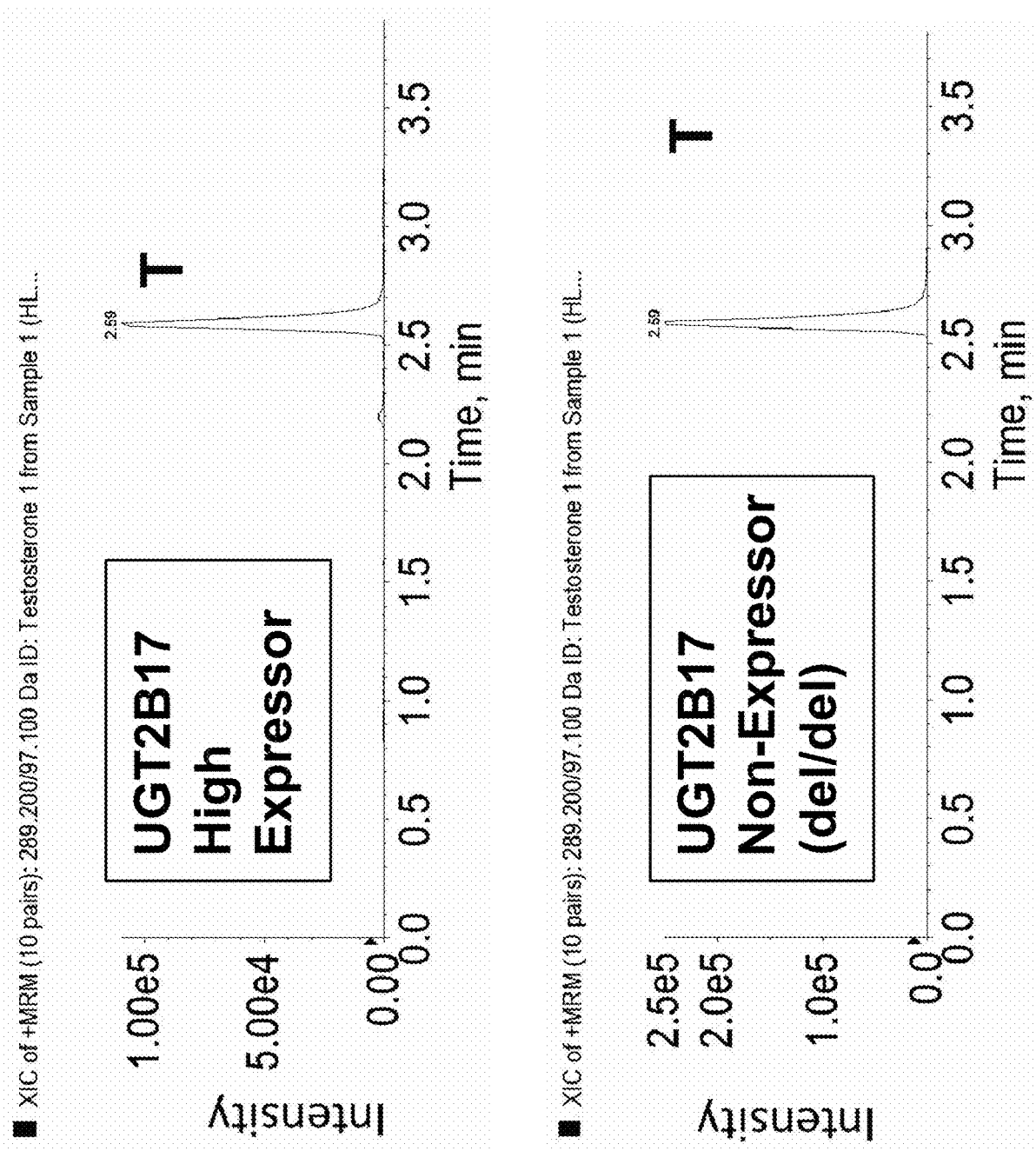
FIG. 10 shows LC/MS traces of testosterone detection (T) and testosterone glucuronide (TG) in a representative UGT2B17 high expresser and UG2B17 non-expresser (del/del). Table shows protein abundance of UGT in the samples.
Figure 10:
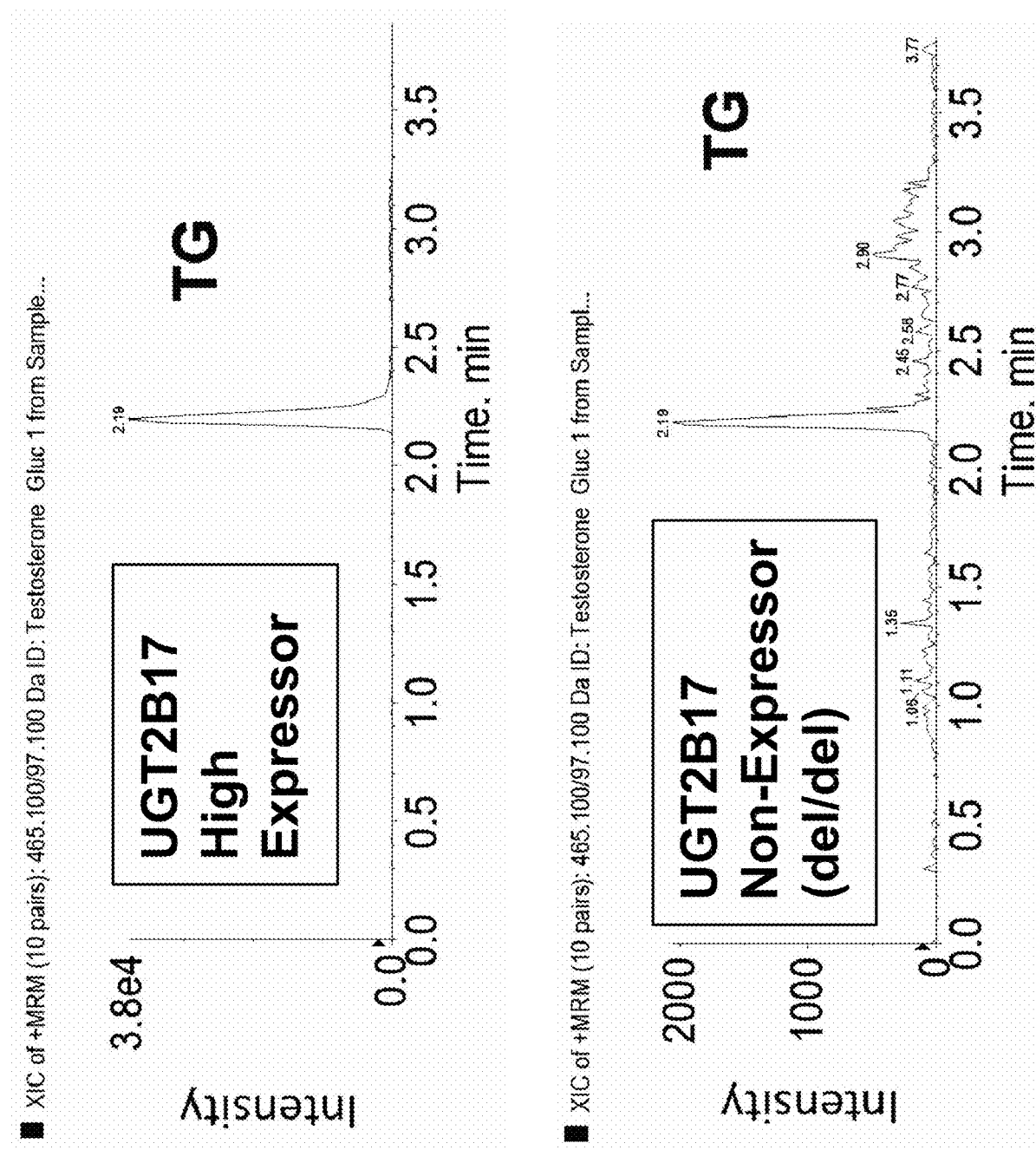

Human liver tissue samples were obtained from the University of Washington Human Liver Bank (Seattle, Wash., USA) (n=29). Protein abundance was measured by total protein quantification, trypsin digestion, and resulting surrogate peptides quantification using AB Sciex 6500 triple quadrupole MS/MS (FIG. 1). Glucuronidation activities of UGT2B15 and UGT2B17 were measured using testosterone as a probe substrate (FIG. 8). The donor demographics are shown in Table 3.

TABLE 3

Donor demographics.

| Gender | Male n = 14 (55%) | | Female n = 13 (45%) |
|---|---|---|---|
| Age | <18 years | 18-65 years | ≥65 years |
| | n = 3 (10%) | n = 24 (83%) | n = 2 (7%) |
| Race | Caucasian | Asian | African American |
| | n = 27 (93%) | n = 1 (3%) | n = 1 (3%) |

Calculation of individual fraction metabolized in UGT2B15 and UGT2B17 was done as follows:
1. Total individual microsomal activity (A)
2. Activity in UGT2B17 del/del samples=UGT2B15 activity (B)
3. Average UGT2B15 activity (C)=[Average B]/[Average UGT2B15 expression]
4. Individual UGT2B15 activity (D)=Individual UGT2B15 expression×(C)
5. Total individual microsomal activity−(D)=individual UGT2B17 activity (E)
6. Individual UGT2B15 fm=D/A
7. Individual UGT2B17 fm=E/A $$CL_{UGT2B17} = CL_{total\ obs} - \frac{\text{Mean } CL_{UGT2B15}\ obs\ (UGT2B17\ del-del\ \text{samples})}{\text{Mean } [E]_{UGT2B15}\ (UGT2B17\ del-del\ \text{samples})} \times [E]_{UGT2B15}$$

Figure 11:
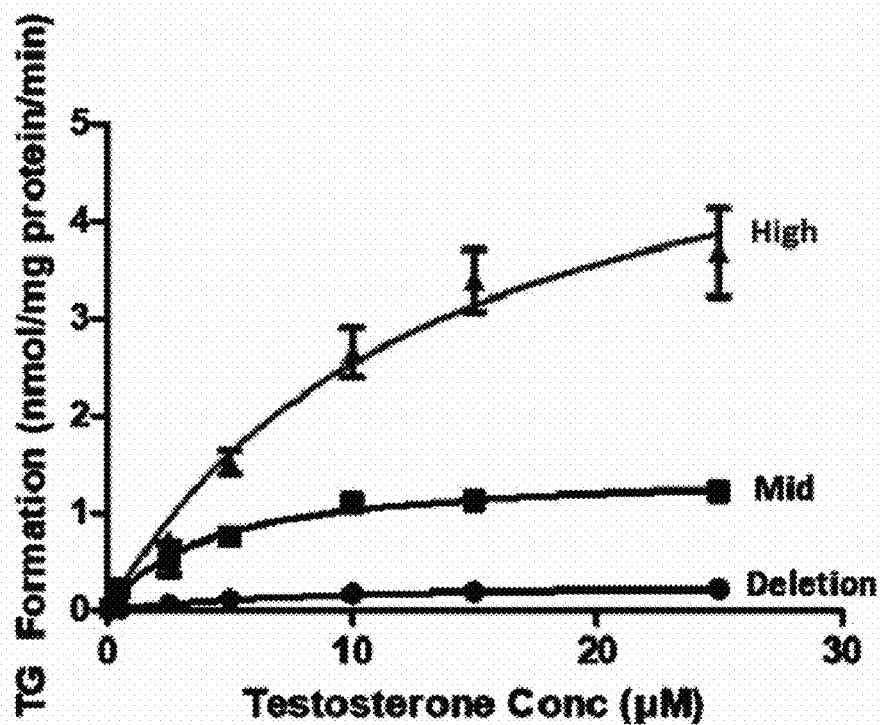
FIG. 11 is a Michaelis-Menten plot of testosterone glucuronide (TG) formation in high (triangles), mid (squares), and null (circles) UGT2B17-expressing human liver microsomes (HLM).
Figure 12A:
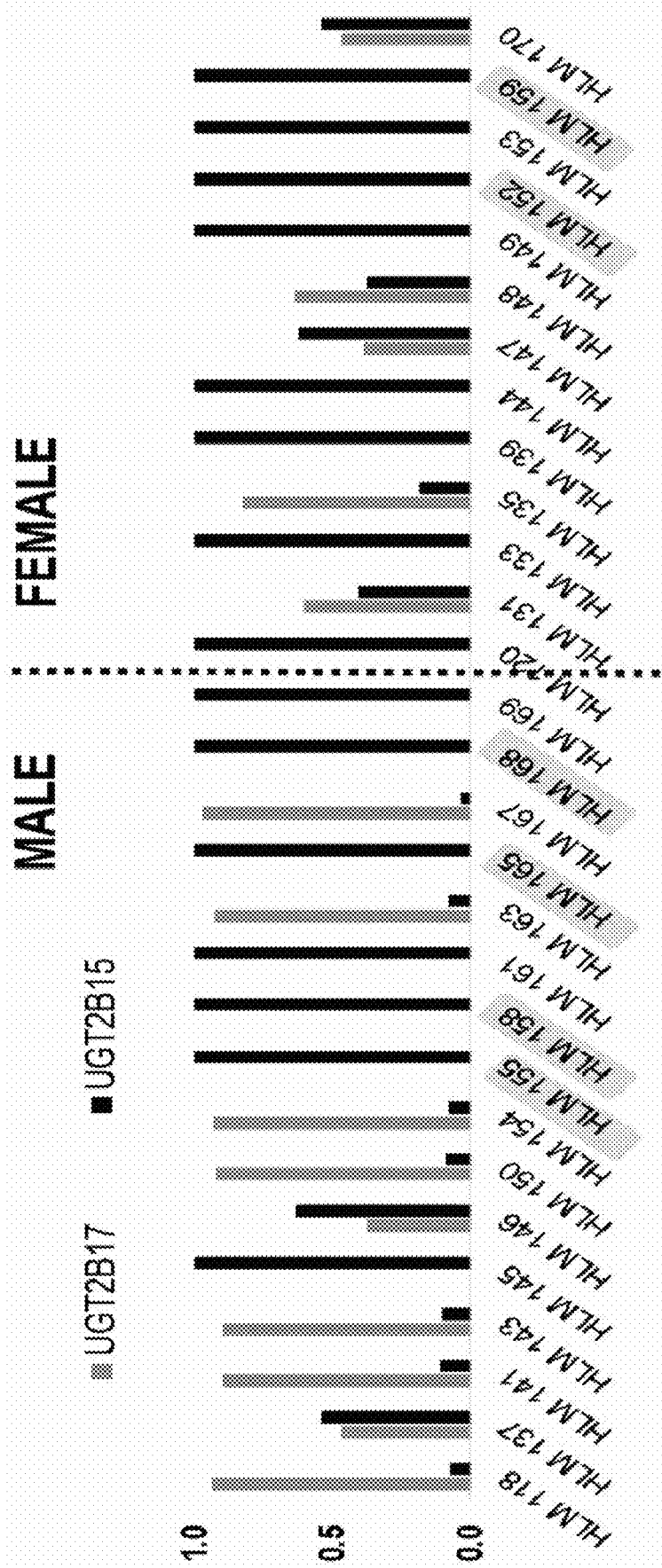
FIGS. 12A and 12B show UGT2B15 and UGT2B17 protein abundance in individual human liver microsomes samples (HLM) (12A) and UGT2B15 and UGT2B17 fractional contribution in TG formation (12B).
Figure 12B:
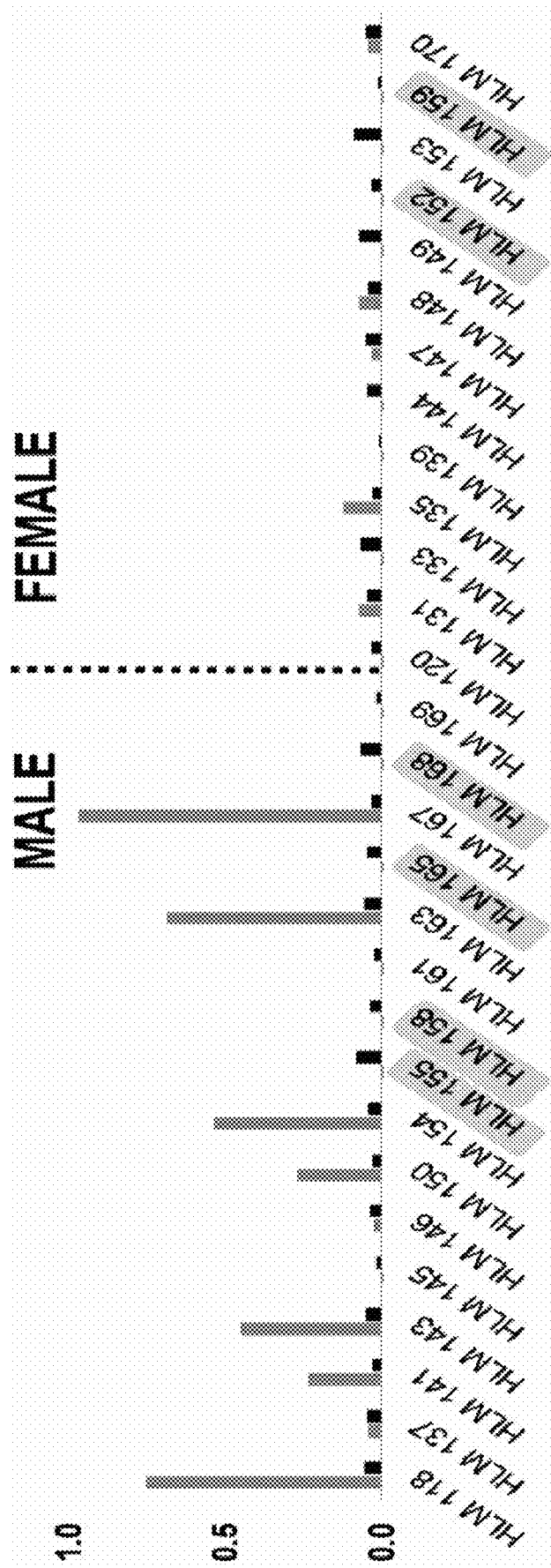
Figure 13A:
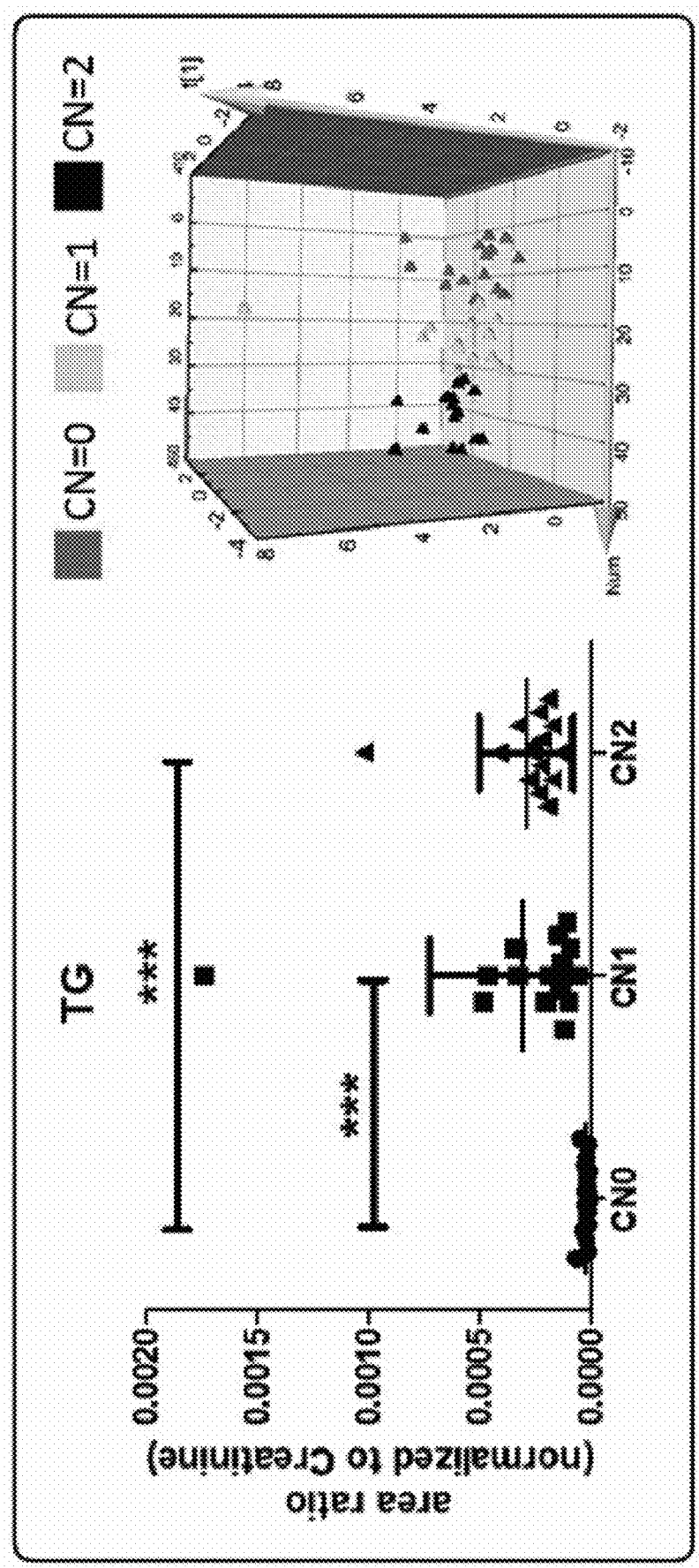
FIGS. 13A-13D show association of UGT2B17 copy number variations (CN=0, 1, and 2) with urine (13A and 13C) and serum (13B and 13D) levels of endogenous biomarker (TG; 13A and 13B) or exogenous marker (dihydroexemestane-glucuronide (DHE-G); 13C and 13D). The urinary TG levels were normalized by creatinine. The PCA plot improved the genotype-phenotype correlation and segregated samples based on the genotype, when multiple UGT2B17-dependent variables, i.e., endogenous compounds (TG, TG/AG and EtioG) or exogenous compounds (exemestane (EXE), DHE, DHE-G, and DHE-G/DHE) were included in the analysis.
Figure 13B:
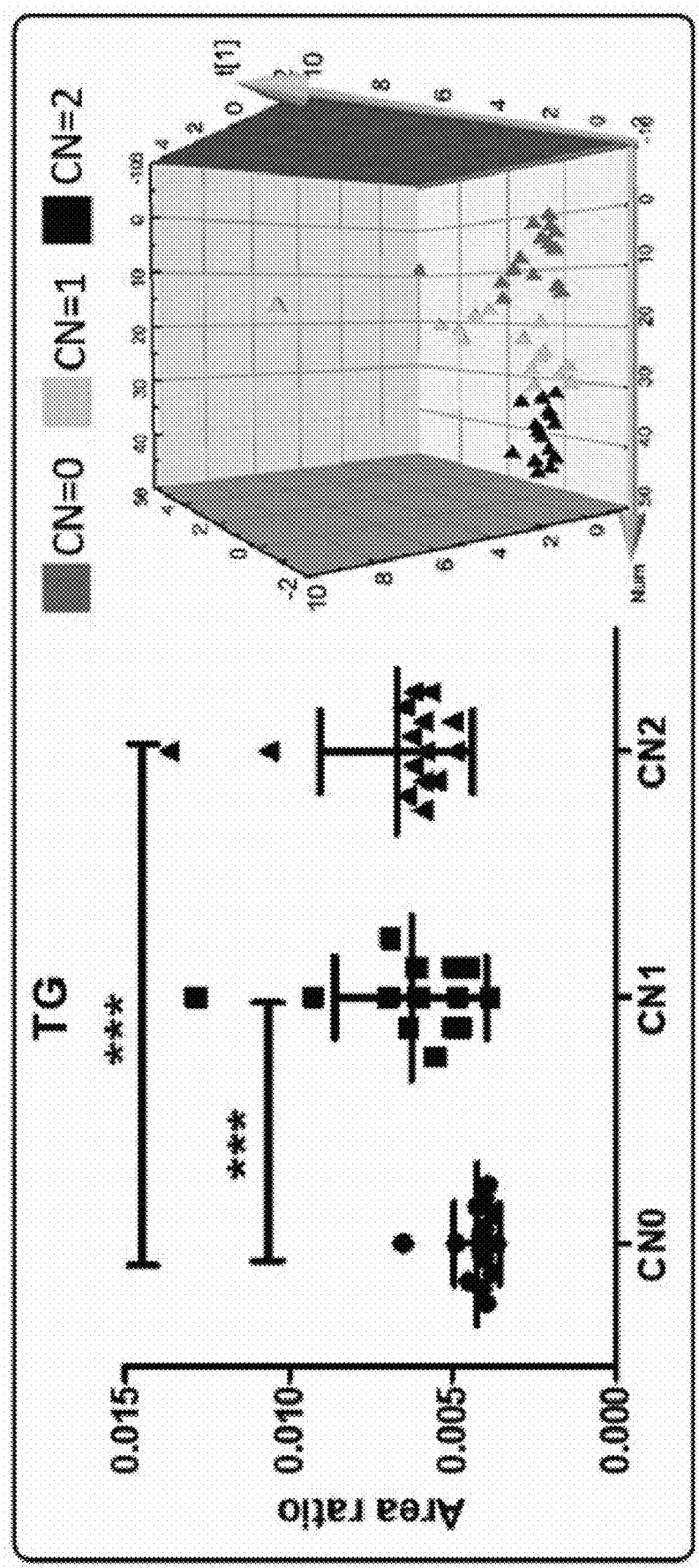
Figure 13C:
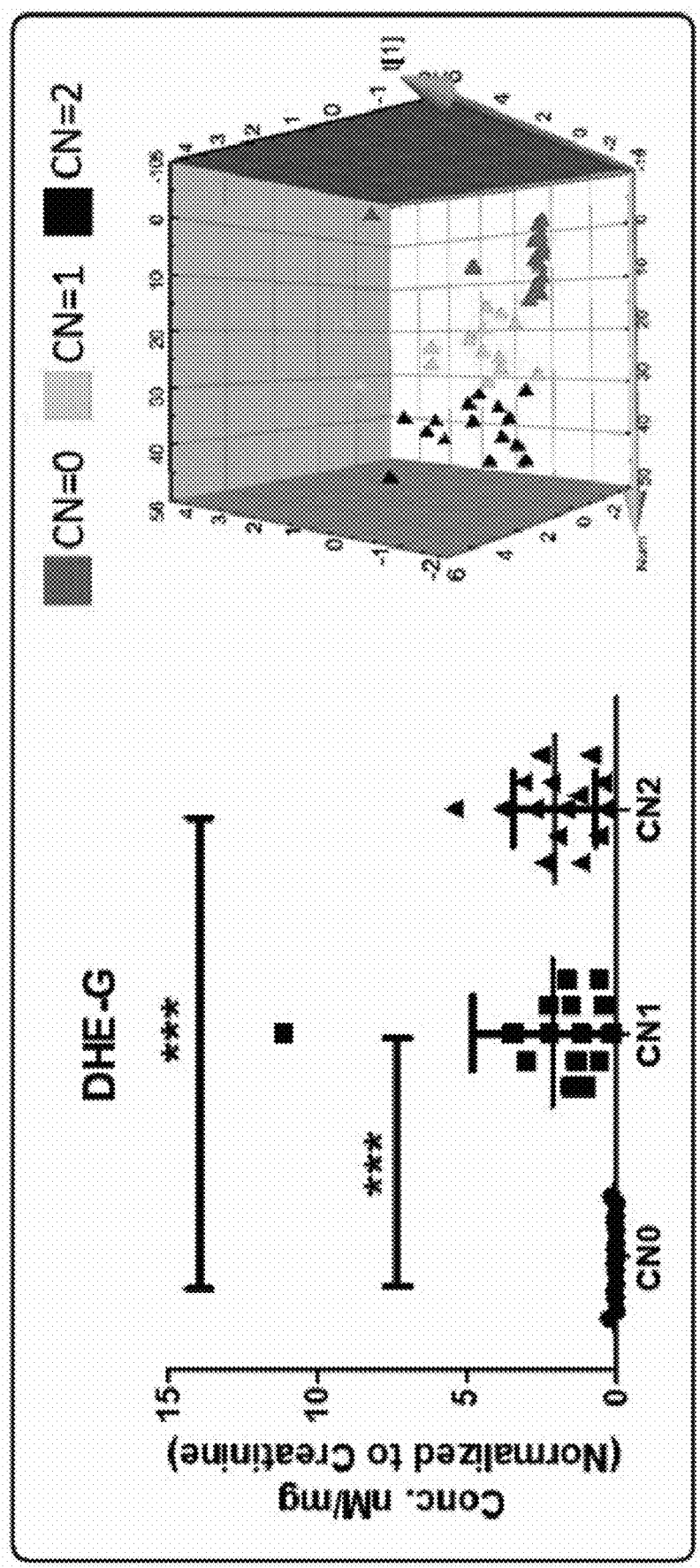
Figure 13D:
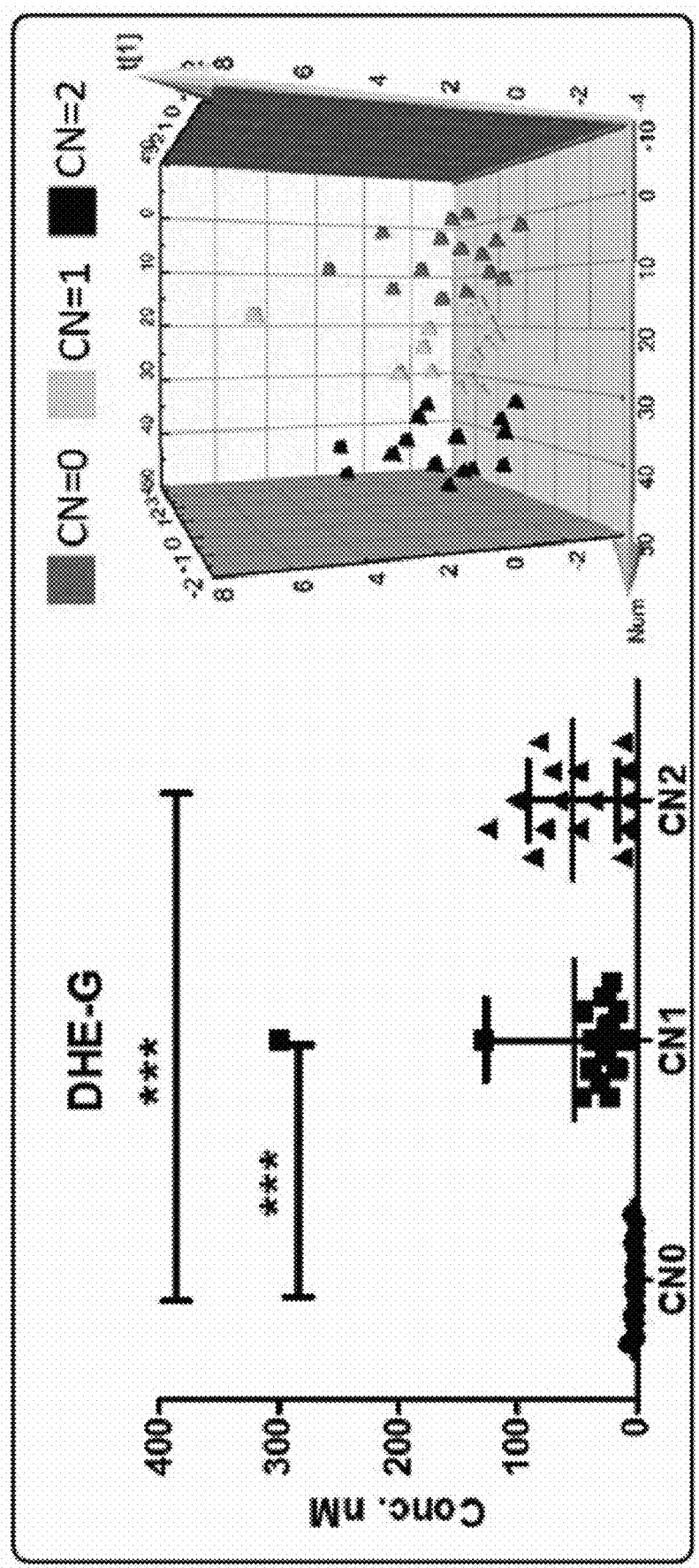

Enzyme kinetic parameters ($V_{max}$ and $K_m$) were determined for UGT2B17 using three human liver microsomes (HLMs) with high, mid, or null UGT2B17 abundance (9.7, 2.3, and 0.06 pmol/mg microsomal protein, respectively) with comparable UGT2B15 abundance (27, 20, and 34 pmol/mg microsomal protein, respectively). Assays were performed in triplicates with varying testosterone concentrations (0.05, 0.25, 0.5, 2.5, 5, 10, 15, 25 μM). Assays were performed in triplicates with 10 μg of protein in 5 mM MgCl2 and 100 mM potassium phosphate buffer (pH 7.4), 0.01% BSA, and 0.1 mg/mL of alamethicin in 100 μL final volume with testosterone. After 15 min of pretreatment on ice, reactions were initiated by addition of 2.5 mM UDP-glucuronic acid (UDPGA), incubated for 30 min (37° C.) at 300 rpm, and terminated using 200 μL of ice-cold acetonitrile containing deuterated TG as validated internal standards. Samples were centrifuged at 10,000 g for 5 min (4° C.). TG was quantified in supernatant by LC-MS/MS. The results are shown in FIG. 11.

Use of Normalized TG (TG/AG) as a UGT2B17 Biomarker

To validate in vivo utility of TG/AG, association of an exogenous marker of UGT2B17, i.e., dihydroexemestatne glucuronide (DHE-G) with TG/AG was performed in a genotype-guided urine samples from patients receiving exemestane (EXE). Genotyping was performed by real-time PCR using a CNV genotyping assay (Hs03185327_c, Life Technologies) with RNase P as a control (Cat #4403326, Life Technologies) using a Bio-Rad CFX384 real-time PCR machine. DHE-G, DHE, TG, and AG were by validated LC-MS/MS methods as described above. The results are shown in FIGS. 13A-13D.

Inhibition of UGT2B17 Activity by Imatinib in HLM

Figure 14:
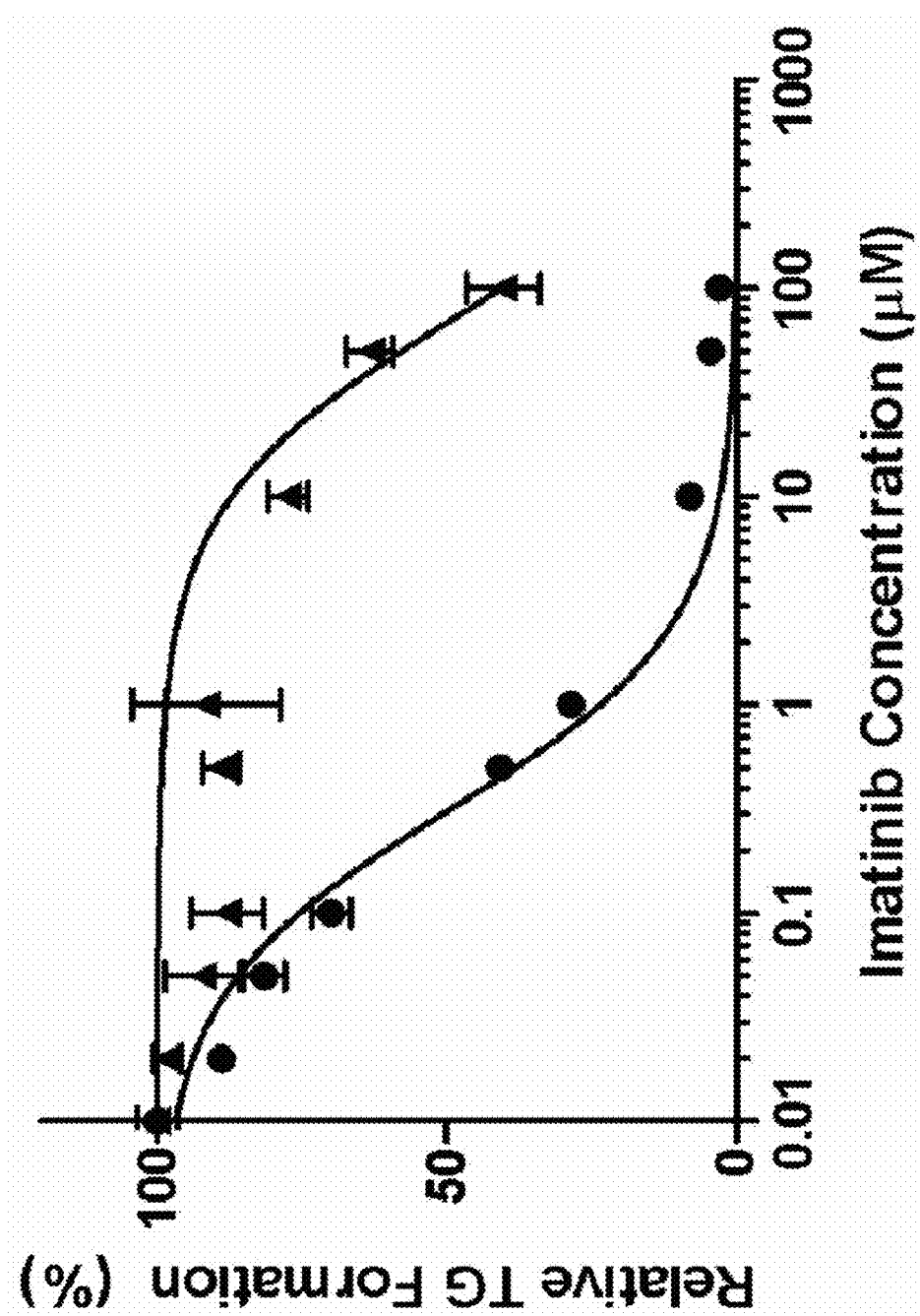
FIG. 14 demonstrates that TG formation is potently inhibited ($IC_{50}$=0.3 µM) by imatinib in HLMs from high expressers of UGT2B17 (circles) as compared to those from UGT2B17-null (triangles). No significant inhibition of oxazepam (UGT2B15) and naloxone (UGT2B7) glucuronidation was noticed in these samples below 20 µM of imatinib.
Figure 15:
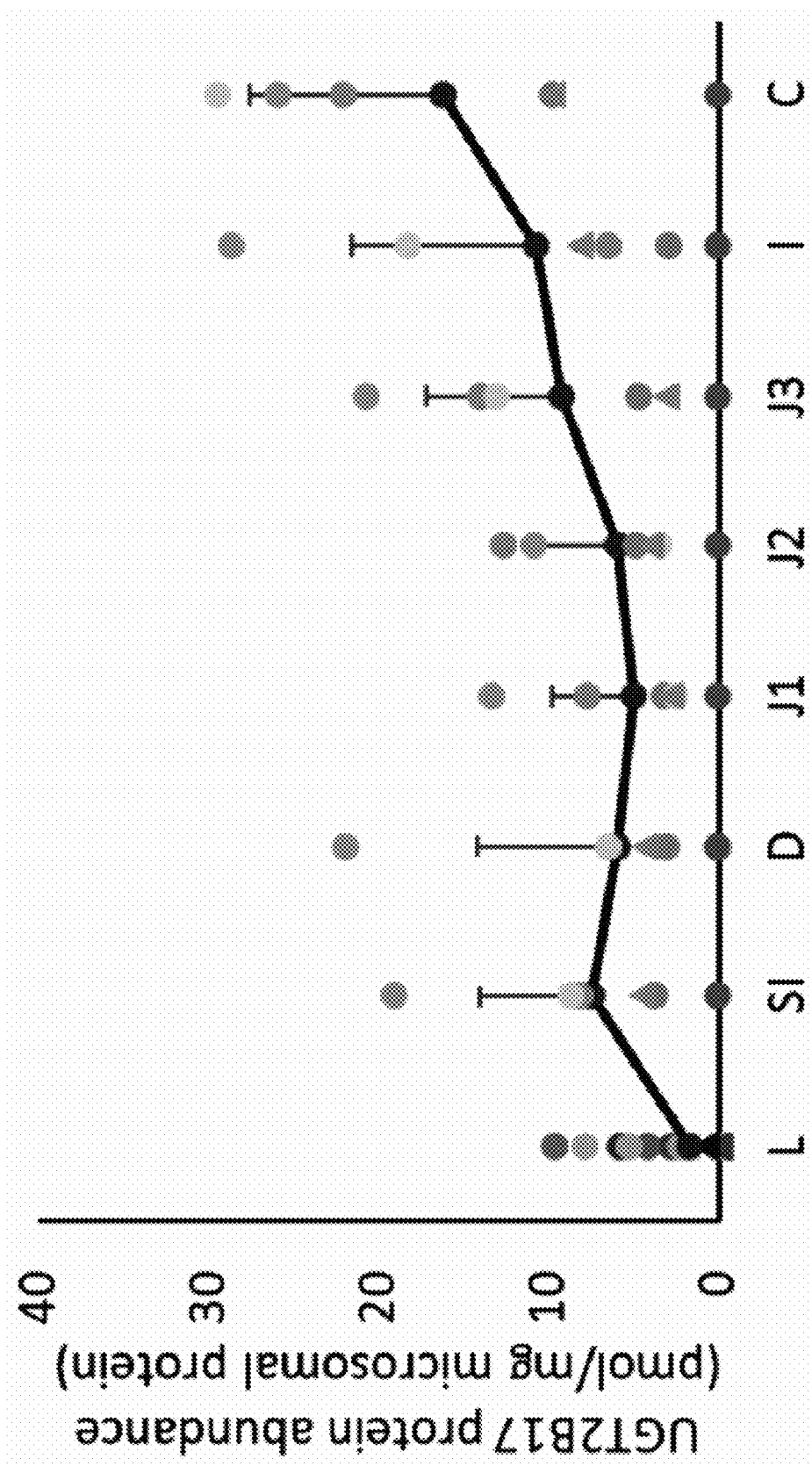
FIG. 15 is a graph of hepatic (L) and intestinal (average (SI) and individual segments) content of UGT2B17 in human tissues (n=6). D, J, I, and C indicate data for matched duodenum (D), jejunum (J1, J2, J3), ileum (I), and colon (C), respectively, for six donors.

UGT2B17 inhibition assays was performed with two HLMs expressing high and below limit of detection (LOD) UGT2B17 abundance (9.7 and 0.06 pmol/mg microsomal protein) with comparable UGT2B15 abundance (27 and 24 pmol/mg microsomal protein). IC$_{50}$ of UGT2B17 inhibition by imatinib was determined by incubating HLM samples with varying inhibitor concentrations (0.01, 0.02, 0.05, 0.1, 0.5, 1, 10, 50, and 100 µM) followed by the testosterone glucuronidation assay in triplicates. UGT2B17 activity was measured with TG formation with 1 µM testosterone. Oxazepam was used as a probe substrate for UGT2B15 activity by measuring oxazepam glucuronide formation (m/z 463.3→287.1, 269.1; DP 70; CE 20) with 10 µM oxazepam. The results are shown in FIG. 14, demonstrating that TG formation is potently inhibited ($IC_{50}$=0.3 µM) by imatinib in HLMs from high expressers of UGT2B17 (circles) as compared to those from UGT2B17-null (triangles). No significant inhibition of oxazepam (UGT2B15) and naloxone (UGT2B7) glucuronidation was noticed in these samples below 20 µM of imatinib.

UGT2B Protein Abundance and Testosterone Glucuronidation in Human Liver and Intestinal Subcellular Fractions Donor-matched intestinal tissue segments (n=6) were procured from Pomeranian Medical University, Szczecin, Poland, and approved by the local Bioethics Committee. Microsome isolation from donor-matched intestinal sections Donor-matched human intestinal microsomes (HIMs) were isolated from different sections of intestine, i.e., duodenum (D), jejunum (J1-J3, three sections), ileum (I), and colon (C), from six individual donors. Tissue samples were disrupted using cell crusher paddles in liquid-nitrogen and HIMs were isolated using protocols from Microsome isolation kit (Abcam, Cambridge, United Kingdom). Total protein was determined by bicinchoninic acid (BCA) assay using the Pierce BCA Protein Assay Kit (Thermo Fisher Scientific, Rockford, Ill.) per manufacturer's protocol.

Membrane proteins were extracted from the cells using Mem-PER Plus Membrane Protein Extraction kit protocol (Rockford, Ill.). Briefly, previously washed and frozen hepatocytes (0.7-6 million) and enterocytes (6.7-37 million) were resuspended with permeabilization buffer (200 or 400 µL), gently mixed, and incubated on a Compact Digital Waving Rotator (Thermo Fisher Scientific, Rockford, Ill.) for 30 min (4° C.) at 300 rpm. Permeabilized cells were centrifuged at 16,000 g for 15 min (4° C.), and resulting supernatant containing cytosolic proteins was removed. Remaining pellet was resuspended with equivolume solubilization buffer, gently mixed, incubated for 60 min at 300 rpm (4° C.), and centrifuged at 16,000 g for 15 min (4° C.). Resulting supernatant containing membrane proteins was collected and total protein quantification was measured with BCA assay (Thermo Fisher Scientific, Rockford, Ill.). Remaining solubilized membrane fraction was stored at −80° C. for subsequent digestion and LC-MS/MS analysis.

UGT2B17 quantification in donor-matched individual HLMs was performed by digesting the membrane proteins using trypsin using an optimized protocol as described in M. Drozdzik et al, Protein abundance of clinically relevant drug-metabolizing enzymes in the human liver and intestine: a comparative analysis in paired tissue specimens. *Clin. Pharmacol. Ther.* (2017).

DISCUSSION AND CONCLUSIONS

The inventors have demonstrated that UGT2B17 protein expression in human liver is highly variable due to effect of genotype, age, and gender, and that UGT2B17, when present, is the predominant enzyme responsible for testosterone glucuronidation. At the same time, UGT2B15 may be an important enzyme for testosterone glucuronidation in UGT2B17 deletion or low-expressing individuals. Because of the high variability in UGT2B17 protein expression, knowing fractional contribution ($f_m$) for both isoforms in testosterone glucuronidation is critical in predicting testosterone drug interactions at individual levels. This approach allows precision dosing of UGT2B17/15 substrate drugs by calculating individualized doses that would eliminate or minimize adverse effects associated with UGT2B17/15 glucuronidation.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The embodiments of the invention in which an exclusive property or privilege is claimed are defined as follows:

1. A method for treating a subject with a pharmaceutical agent that is at least partially metabolized by UGT2B17-dependent glucuronidation, comprising the steps of:
    determining the activity of UGT2B17 according to the presence of one or more endogenous biomarkers of UGT2B17 activity in a sample obtained from the subject, wherein the one or more biomarkers of UGT2B17 activity is a ratio of a concentration of testosterone glucuronide (TG) to a concentration of aldosterone glucuronide (AG) in the sample;
    identifying an effective therapeutic amount of a pharmaceutical agent, wherein at least a portion of the pharmaceutical agent is metabolized by UGT2B17-dependent glucuronidation, by adjusting the portion of the agent metabolized by UGT2B17 proportionally to the UGT2B17 activity; and
    administering the effective therapeutic amount of the pharmaceutical agent to the subject in need thereof.

2. The method of claim 1, wherein the pharmaceutical agent is vorinostat, exemestane, or clopidogrel.

3. The method of claim 1, wherein the sample is blood, urine, plasma, or serum.

4. The method of claim 1, wherein the determining the presence of one or more endogenous biomarkers of UGT2B17 activity in the sample is done by LC/MS.

5. The method of claim 1, wherein the effective therapeutic amount is an amount that does not result in hepatotoxicity caused by UGT2B17 mediated glucuronidation in the subject.

* * * * *